(12) United States Patent
Cohen et al.

(10) Patent No.: US 10,073,948 B2
(45) Date of Patent: Sep. 11, 2018

(54) MEDICAL DATA MANAGEMENT SYSTEM AND PROCESS

(71) Applicant: Medtronic MiniMed, Inc., Northridge, CA (US)

(72) Inventors: Gary Cohen, Sherman Oaks, CA (US); Joel Goldsmith, Studio City, CA (US); Pam S. Roller, Valencia, CA (US); Sanford Widran, Sherman Oaks, CA (US); George W. Patterson, Westlake Village, CA (US); James R. Daugherty, Northridge, CA (US); William P. Van Antwerp, Valencia, CA (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 1134 days.

(21) Appl. No.: 14/213,824

(22) Filed: Mar. 14, 2014

(65) Prior Publication Data

US 2014/0200923 A1  Jul. 17, 2014

Related U.S. Application Data

(62) Division of application No. 13/457,334, filed on Apr. 26, 2012, now Pat. No. 8,715,180, which is a division
(Continued)

(51) Int. Cl.
*G06F 19/00* (2018.01)
*A61M 5/172* (2006.01)
(Continued)

(52) U.S. Cl.
CPC ......... *G06F 19/328* (2013.01); *A61M 5/1723* (2013.01); *G06F 19/325* (2013.01);
(Continued)

(58) Field of Classification Search
CPC ............................. G06F 19/322; G06Q 50/22
See application file for complete search history.

(56) References Cited

U.S. PATENT DOCUMENTS 5,544,649 A   8/1996 David et al.
5,583,758 A   12/1996 McIlroy et al.
(Continued)

FOREIGN PATENT DOCUMENTS

WO   WO-02/073503   9/2002
WO   WO-02/099600   12/2002
(Continued)

OTHER PUBLICATIONS

U.S. Office Action dated Oct. 28, 2008, from related U.S. Appl. No. 10/913,149.
(Continued)

*Primary Examiner* — Scott T Luan
(74) *Attorney, Agent, or Firm* — Foley & Lardner LLP

(57) ABSTRACT

Systems and processes for managing data relating to one or more medical or biological conditions of a plurality of subjects (such as patients) over a wide area network, such as the Internet, may be employed for diabetes subjects or subjects with other medical conditions requiring monitoring and/or treatment over time. Such systems and processes provide various functions for several types of users, including patients or subject-users, healthcare provider-users and payor entity-users and combinations thereof, which allow for improved treatment and medical data management of individual subjects and groups of subjects and which allow collection and analysis of aggregate data from many subject sources, for improving overall healthcare practices of providers and subjects (e.g., patients).

21 Claims, 7 Drawing Sheets

Related U.S. Application Data of application No. 10/913,149, filed on Aug. 6, 2004, now Pat. No. 8,313,433.

(51) Int. Cl.

| | |
|---|---|
| *G06Q 50/22* | (2018.01) |
| *G16H 10/60* | (2018.01) |
| *G16H 15/00* | (2018.01) |
| *A61B 5/00* | (2006.01) |
| *A61B 5/145* | (2006.01) |
| *G16H 50/70* | (2018.01) |
| *G16H 50/20* | (2018.01) |

(52) U.S. Cl.
CPC ...... *G06F 19/3468* (2013.01); *G06F 19/3481* (2013.01); *G06Q 50/22* (2013.01); *G16H 10/60* (2018.01); *G16H 15/00* (2018.01); *A61B 5/0002* (2013.01); *A61B 5/14532* (2013.01); *A61B 2560/0271* (2013.01); *A61M 2205/3553* (2013.01); *A61M 2205/52* (2013.01); *G06F 2221/2113* (2013.01); *G06F 2221/2141* (2013.01); *G16H 50/20* (2018.01); *G16H 50/70* (2018.01)

(56) References Cited

U.S. PATENT DOCUMENTS

| | | | |
|---|---|---|---|
| 5,772,635 | A | 6/1998 | Dastur et al. |
| 6,230,142 | B1 | 5/2001 | Benigno et al. |
| 6,249,705 | B1 | 6/2001 | Snell |
| 6,641,533 | B2 | 11/2003 | Causey et al. |
| 6,641,553 | B1 | 11/2003 | Chee et al. |
| 6,958,705 | B2 | 10/2005 | Lebel et al. |
| 7,077,806 | B2 | 7/2006 | Ackermann et al. |
| 7,191,006 | B2 | 3/2007 | Hu et al. |
| 7,324,949 | B2 | 1/2008 | Bristol |
| 7,433,853 | B2 | 10/2008 | Brockway et al. |
| 7,645,258 | B2 | 1/2010 | White et al. |
| 7,678,071 | B2 | 3/2010 | Lebel et al. |
| 7,698,156 | B2 | 4/2010 | Martucci et al. |
| 7,756,721 | B1 | 7/2010 | Falchuk et al. |
| 2001/0023360 | A1 | 9/2001 | Nelson et al. |
| 2002/0004727 | A1 | 1/2002 | Knaus et al. |
| 2002/0010679 | A1 | 1/2002 | Felsher |
| 2002/0019586 | A1 | 2/2002 | Teller et al. |
| 2002/0042726 | A1 | 4/2002 | Mayaud |
| 2002/0138155 | A1 | 9/2002 | Bristol |
| 2002/0169635 | A1 | 11/2002 | Shillingburg |
| 2002/0169636 | A1 | 11/2002 | Eggers et al. |
| 2002/0181680 | A1 | 12/2002 | Linder et al. |
| 2002/0193679 | A1 | 12/2002 | Malave et al. |
| 2003/0023461 | A1 | 1/2003 | Quintanilla et al. |
| 2003/0028082 | A1 | 2/2003 | Thompson |
| 2003/0060765 | A1 | 3/2003 | Campbell et al. |
| 2003/0149597 | A1 | 8/2003 | Zaleski |
| 2003/0153819 | A1 | 8/2003 | Iliff |
| 2004/0039263 | A1 | 2/2004 | Bardy |
| 2004/0039265 | A1 | 2/2004 | Bardy |
| 2004/0078238 | A1 | 4/2004 | Thomas et al. |
| 2004/0117215 | A1 | 6/2004 | Marchosky |
| 2004/0128161 | A1 | 7/2004 | Mazar et al. |
| 2004/0167465 | A1 | 8/2004 | Mihai et al. |
| 2004/0172287 | A1 | 9/2004 | O'Toole et al. |
| 2004/0172305 | A1 | 9/2004 | Soerensen et al. |
| 2004/0181433 | A1 | 9/2004 | Blair |
| 2004/0193025 | A1 | 9/2004 | Steil et al. |
| 2004/0193448 | A1 | 9/2004 | Woodbridge et al. |
| 2004/0215981 | A1 | 10/2004 | Ricciardi et al. |
| 2004/0260478 | A1 | 12/2004 | Schwamm |
| 2005/0010448 | A1 | 1/2005 | Mattera |
| 2005/0022274 | A1 | 1/2005 | Campbell et al. |
| 2005/0038680 | A1 | 2/2005 | McMahon |
| 2005/0065464 | A1 | 3/2005 | Talbot et al. |
| 2005/0065824 | A1 | 3/2005 | Kohan |
| 2005/0071189 | A1 | 3/2005 | Blake et al. |
| 2005/0075543 | A1 | 4/2005 | Calabrese |
| 2005/0113649 | A1 | 5/2005 | Bergantino |
| 2005/0119914 | A1 | 6/2005 | Batch |
| 2005/0165623 | A1 | 7/2005 | Landi et al. |
| 2005/0182661 | A1 | 8/2005 | Allard et al. |
| 2005/0215867 | A1 | 9/2005 | Grigsby et al. |
| 2005/0234740 | A1* | 10/2005 | Krishnan ......... G06Q 10/06398 705/2 |
| 2005/0277912 | A1 | 12/2005 | John |
| 2005/0278073 | A1 | 12/2005 | Roth |
| 2006/0010090 | A1 | 1/2006 | Brockway et al. |
| 2006/0026040 | A1* | 2/2006 | Reeves ................ G06F 19/321 705/3 |
| 2006/0026205 | A1 | 2/2006 | Butterfield |
| 2006/0235280 | A1 | 10/2006 | Vonk et al. |
| 2007/0118397 | A1 | 5/2007 | Williams et al. |

FOREIGN PATENT DOCUMENTS

| | | |
|---|---|---|
| WO | WO-03/014735 | 2/2003 |
| WO | WO-2004/009161 | 1/2004 |

OTHER PUBLICATIONS

U.S. Office Action dated Aug. 3, 2009, from related U.S. Appl. No. 10/913,149.
U.S. Office Action dated Mar. 29, 2010, from related U.S. Appl. No. 10/913,149.
U.S. Office Action dated May 24, 2011, from related U.S. Appl. No. 10/913,149.
U.S. Office Action dated Oct. 21, 2011, from related U.S. Appl. No. 10/913,149.
U.S. Notice of Allowance dated Jul. 26, 2012, from related U.S. Appl. No. 10/913,149.
U.S. Office Action dated Sep. 17, 2012, from related U.S. Appl. No. 13/457,334.
U.S. Office Action dated May 7, 2013, from related U.S. Appl. No. 13/457,334.
U.S. Notice of Allowance dated Dec. 24, 2013, from related U.S. Appl. No. 13/457,334.
International Search Report dated Mar. 6, 2006, from related International Application No. PCT/US2005/024311.
EPO Official Action dated May 14, 2008, from related EP patent application No. 05779556.9.
EPO Official Action dated Jul. 6, 2009, from related EP patent application No. 05779556.9.
EPO Official Action dated Jan. 20, 2011, from related EP patent application No. 05779556.9.
EPO Official Action dated Jun. 12, 2012, from related EP patent application No. 05779556.9.
EPO Official Action dated Aug. 8, 2013, from related EP patent application No. 05779556.9.
Japanese Office Action, with English translation, dated Oct. 26, 2010, from related Japanese Patent Application No. 2007-524812.

* cited by examiner

MEDICAL DATA MANAGEMENT SYSTEM AND PROCESS

CROSS-REFERENCE TO RELATED PATENT APPLICATIONS

This application is a Divisional of U.S. application Ser. No. 13/457,334, filed Apr. 26, 2012, which is a Divisional of U.S. application Ser. No. 10/913,149, filed Aug. 6, 2004, each of which is incorporated herein by reference in its entirety.

FIELD OF THE INVENTION

Embodiments of the invention relate to systems and processes for managing data relating to one or more medical or biological conditions of a plurality of subjects (such as patients) over a wide area network, such as the Internet, and, particular embodiments relate to such systems and processes for diabetes subjects. Embodiments of such systems and processes provide various functions for several types of users, including patients or subject-users, healthcare provider-users and payor entity-users and combinations thereof, which allow for improved treatment and medical data management of individual subjects and groups of subjects and which allow collection and analysis of aggregate data from many subject sources, for improving overall healthcare practices of providers and subjects (e.g., patients).

BACKGROUND OF THE INVENTION

Traditionally, many modern programmable medical devices, for example, medical infusion pumps, include internal memory for generating and storing data representing actual device operation over a period of time. The stored data may be reviewed from the medical device on a periodic basis by medical personnel, so that the subject's condition and treatment regimen can be closely monitored, and the medical device may be reprogrammed as needed. However, to retrieve data from certain prior medical devices, such as infusion pump, the subject would have been required to make regular visits to a medical treatment facility.

To overcome this drawback, raw data has been transferred from an infusion pump to another data storage and/or processing device. An example of a data transfer system for an infusion pump is disclosed in U.S. Pat. No. 5,376,070 issued Dec. 27, 1994 to Purvis et al. and is entitled "Data transfer System for an Infusion Pump," which is herein incorporated by reference. This device relates to a relatively simple and effective data transfer system that is designed for retrieving data from, and sending program data to, a medication infusion pump. The data transfer system is particularly suited for remote data transfer and/or reprogramming of the infusion pump.

Another communication system for use with an infusion pump, analyte monitor, analyte meter or the like is described in published PCT application PCT/US99/22993. That system includes a communication station having a cradle for receiving a pump, meter or monitor, and for interfacing with a personal computer or the like. By connecting the pump, meter or monitor in communication with a personal computer, programming and instructions may be communicated from the computer to the medical device and data may be transferred from the medical device to the computer.

While some systems have been developed for retrieving subject information from a subject's medical device, there is a need in the industry for a more comprehensive system capable of collecting and managing subject information for multiple subjects, including multiple subjects with a plurality of different types of medical devices (different manufacturers, different models from the same manufacturer or different functional devices). There is also a need in the industry for such a system that provides capabilities for analyzing conglomerate data from multiple subjects, to develop or modify treatment plans for a particular subject or a group of subjects. There is a further need in the industry for such a system that allows a healthcare provider to issue a modifying treatment plan, for example, based on an algorithm or other scheme that determines a treatment modification based on subject information received from a particular subject or from a defined group of subjects. There is also a need in the industry for such a system that provides capabilities for complying (or showing compliance) with government regulations, industry standards or policies regarding, for example, security of personalized subject information, proper record keeping, automatic updating of user's software, and the like. There is yet a further need in the industry for a system that provides sufficient information to a healthcare provider, such as past subject information regarding a subject or group of subjects, to establish a starting point or initial settings for a new medical device that is about to be issued to a subject or group of subjects.

SUMMARY OF THE INVENTION

Embodiments of the invention relate to medical data management systems and processes for managing data relating to one or more medical or biological conditions of at least one (or a plurality of) subject(s) over a wide area network, such as the Internet, and which address one, some or all of the industry needs noted above. Examples of such systems and processes may be configured for diabetes subjects, cardiac subjects, cancer subjects, HIV subjects, subjects with other disease, infection or other controllable condition.

Embodiments of such systems and processes provide various functions for subject-users, healthcare provider-users and payor entity-users and combinations thereof, for improved treatment and medical data management for individual subjects and/or groups of subjects. For example, embodiments of the system allow collection and analysis of aggregate data from many subject sources, for improving overall healthcare practices for individual patents and/or groups of subjects.

According to embodiments of the present invention, a medical data management system may be configured with a group of software modules running on one or more servers connected to a wide-area network, such as the Internet. Users may communicate with the medical data management system over the Internet, for example, using a conventional personal computer (PC or other suitable network device) having conventional browser software and/or other software for interacting with the system. Subject-users or healthcare provider-users may connect subject support devices (such as infusion pumps, meters, biological sensors, pacemakers, other electronic cardiactric aids or the like) to their user-side computers, for communicating information between the subject support devices and the medical data management system. In this manner, the system may collect and manage data from at least one user (and, in more comprehensive embodiments, from a plurality of users) and provide a number of services individually or inter-related to each other.

By providing a centralized medical data management system, healthcare providers and subjects may readily store and later access medical information relating to the subjects, for example, to analyze historical information regarding a subject's biological condition, operation of the subject support device, treatment, treatment results, personal habits, or the like. Based on such historical data, the healthcare provider and/or subject may be able to recognize trends, beneficial practices, detrimental practices or the like and, thereby, adjust or design treatment plans that take advantage of beneficial trends and practices and avoids detrimental trends and practices.

The medical data management system may include software for generating or otherwise providing reports containing information received from a subject, a group of subjects or multiple groups of subjects. In this manner, a subject or a subject's healthcare provider may readily access formatted reports of information regarding the subject's condition, historical condition, the subject support device operation or condition, or the like, or similar information regarding one or more defined groups of subjects. The reports may be formatted in various pre-defined formats provided by the system. Alternatively or in addition, the system may allow users to design their own report format (including determining what type of information to include in the report and how the information is displayed).

The centralization of the data collection and management for one or more subjects allows a centralization of the report generation and formatting, such that multiple users may become familiar with the same one or more preferred types of reports (with certain types of data content and/or format), for example, in the case of a healthcare provider-user who prefers that all of their subjects use a particular type of report. Furthermore, healthcare provider-users may recommend or design reports (content and/or format) to accommodate individual subjects or groups of subjects. Centralization of the report generating and formatting tools also allows the system to provide all users with the most updated selection of types of reports, including types of content or format options.

In more comprehensive embodiments in which the system collects and manages medical data from a plurality of subjects, the system may provide a powerful tool for analyzing and providing reports on trends and practices of groups of subjects. The ability to collect, arrange in various reports (of various content and format types) allows users to analyze aggregate information from a relatively large population of subject users. This can provide important improvements in the capabilities for adjusting and designing treatment plans for individual subjects or groups of subjects. Such capabilities may be increased significantly in system embodiments that support multiple different types of subject support devices (for example, devices made by different manufacturers, different models of devices from the same manufacturer or different functional devices), in which case the aggregate data collected from multiple subject-users need not be limited to subject-user's that have a particular type of subject support device.

Depending upon the embodiment and environment of use, subject groups may be defined by certain common characteristics or similarities in the subject's biological condition or state. For example, such groups may be defined as diabetes subjects, coronary subjects, subjects with diabetes type 1, subjects with diabetes type 2, female subjects with diabetes, male subjects with diabetes, subjects under or over a specified age, or any other suitable group characteristic. Also or alternatively, subject groups may be defined by characteristics or similarities in subject data received by the system from a subject's support device or from a manual data entry. Such groups may be defined as, for example, subjects that use a particular type of subject support device (by function, manufacturer, model, or other characteristic), subjects that test blood-glucose levels more than once a day, subjects that exercise at least once a day, or any other suitable group characteristic. Further groups may be defined by combinations of characteristics (for example, female subjects with type 2 diabetes who are under the age of 13 and test blood levels less than once a day).

Analysis of the behavior and treatment results of defined groups of subjects can assist a healthcare provider and/or subject in designing or improving a treatment plan for the subject or for a group of subjects. An analysis of common behaviors, treatments or treatment results of subjects in a particular group or set of groups may allow the healthcare provider and/or subject to match or diverge that subject's treatment or behavior to the treatment or behavior of the subject's in the group. Similarly, a healthcare provider may analyze the behaviors, treatments or treatment results of subjects in one or more groups to develop or improve treatment plans for that or another group of subjects (all subjects within the group). In this manner, the treatment plan for a given subject within a defined group or for some or all subjects of a group may be developed or improved, based on an analysis of historical data for the group.

In further example embodiments, a healthcare provider-user may issue a treatment plan for a subject or for a group of subjects, where the treatment plan includes modifications to a subject's treatment, if the subject's information (data from the subject's support device or from a manual input) meets at least one (or multiple) event(s) defined in the treatment plan. In this regard, a healthcare provider may provide a treatment plan that adjusts or modifies, automatically, with the subjects behavior or condition (or with the condition or operation of the subject's support device, with environmental conditions, or other conditions defined in the treatment plan).

Further embodiments of the system also allow a healthcare provider to communicate payment request information for submission to a payor entity-user. Payor entity-users may communicate with the system to obtain payment request information from healthcare provider users who provided treatments to subjects. The payor entity-user also may access subject information and/or generate (or otherwise obtain) reports containing information corresponding to the subject who received the treatment, for example, to verify payment requests.

Thus, embodiments of the system allow for the collection and management of medical data from a relatively large number and/or variety of subject-users, in a centralized manner. Such centralized medical data collection and management may be conducted with user-friendly, convenient Internet interfaces. The system may employ one or more websites that provide easy access to a variety of information and services for improving the treatment and care of medical subjects.

Centralizing data management for many subjects in a user-friendly, Internet-connected system may improve the management of user's software resources, for example, by providing a mechanism to update user software, provide new software or new generations/versions of a given software, or provide new or revised program data automatically (or by user request). Thus, users will be more likely to have the most recent, updated versions of software, resources or data available on the system. Also, users may be able to cooperate together an improved manner, such as by being able to generate the same type of reports or by allowing one user to define a report format (content and/or layout) for another user. For example, a subject-user, a healthcare provider-user and/or a payor entity-user may be able to generate the same reports on their respective computers, to assist the users in explaining treatments or payment benefits. Moreover, a healthcare provider-user who is familiar with the system and available reports may more readily assist a subject-user in the generation or analysis of the reports.

Also, a centralized data management system may provide improved security and data safeguarding capabilities and can simplify and reduce the cost of implementing security measures. Another benefit that may be available with a centralized data management system is the ability to deliver training materials or other resources to users, as needed (and as a need is perceived). Other benefits that may be available with a centralized medical data management system include the ability to collect, organize and communicate information employed for showing compliance with the government regulations, industry standards, or industry or internal, policies (including but not limited to the Federal Food and Drug Administration (FDA))

Furthermore, a centralized data management system may allow the collection and management of historical subject information, for access by a healthcare provider (or other personnel) for designing a starting point or initial settings for a medical device. Thus, a subject (or group of subjects) receiving a new medical device may have the medical device programmed or pre-programmed to provide an initial treatment (or have other initial settings), based on historical data collected by the data management system.

Thus, several features of the system may be employed individually or in combination to improve subject care for individual subject-users. In addition, the system may be employed to collect aggregate data from many different subjects and/or subject support devices (or different defined groups of subjects and/or defined groups of subject support devices). Aggregate data of many subject sources (or groups) may be analyzed to develop best practices for treatment or lifestyle of individual subjects, defined groups of subjects or all subjects. By providing a system with the capability of interfacing with multiple different types of subject support devices, data from different types or different groups of subjects may be obtained by the system, to further improve the aggregate data capabilities of the system. For example, by employing suitable interface software and electronics, subject support devices made from multiple different manufacturers or multiple different models of a subject support device of a given manufacturer may be coupled to communicate with the system, to provide an expanded capability to collect and analyze aggregate data and develop better treatment practices for a greater number of subjects.

These and other advantages will become apparent from the following drawings and detailed description of example embodiments.

DETAILED DESCRIPTION OF THE PREFERRED EMBODIMENTS

The following detailed description is of the best presently contemplated mode of implementing embodiments of the invention. This description is not to be taken in a limiting sense, but is made merely for the purpose of illustrating general principles of embodiments of the invention. The scope of the invention is best defined by the appended claims.

Embodiments of the present invention employ software components that operate with network devices and related hardware to manage the movement of electronic information, store the information in an organized format and provide controlled, worldwide access over the Internet to the information. The information may relate to one or more medical conditions and the system and services may involve medical subjects, healthcare providers, and/or healthcare payer entities.

Figure 1:
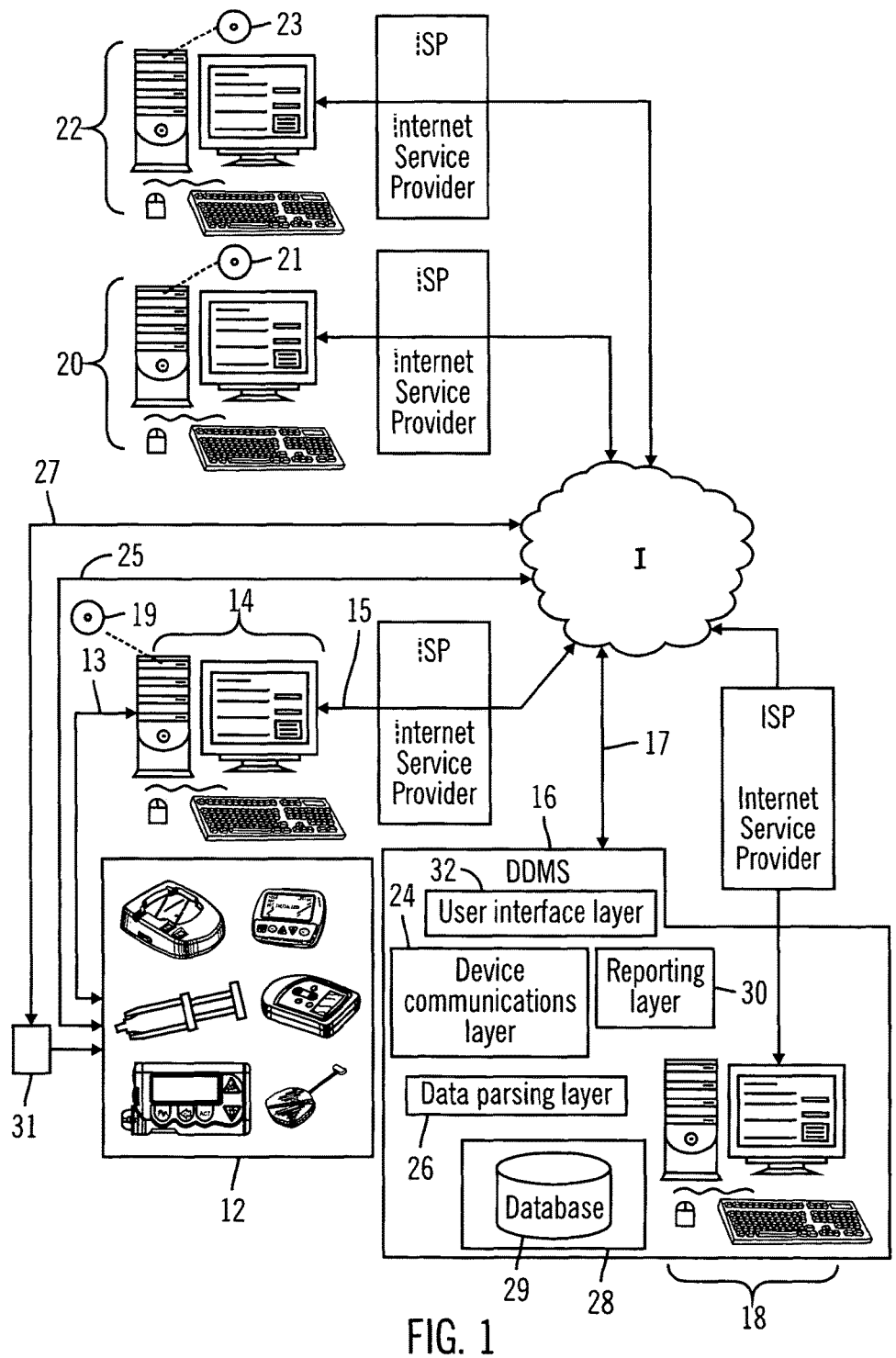
FIG. 1 is a generalized schematic diagram of a system environment according to an embodiment of the present invention.

For example, embodiments of the invention relate to systems and processes for managing data regarding medical or biological conditions of a plurality of subjects over a wide area network, such as the Internet. Embodiments of the system are particularly suited for collecting and managing data relating to one or more controllable medical or biological conditions, where the managed data may be used to provide feedback controls for treating the medical or biological condition. For example and without limitation, such systems and processes may be configured for diabetes subjects, cardiac subjects, cancer subjects, HIV subjects, subjects with other disease, infection or other controllable condition, or various combinations thereof Hardware System Environment:

A generalized diagram of a system 10 according to embodiments of the present invention is shown in FIG. 1. Example embodiments of the system 10 are described herein with reference to use in medical service contexts. In such embodiments, at least one (preferably multiple) subjects or subjects are each provided with at least one (or multiple) subject or subject support device(s) 12.

A subject support device 12 may comprise a device that is designed to be carried by a subject or otherwise be in the subject's locality and provide a function, such as a treatment, metering, monitoring or sensing function on the subject or subject's environment. In certain embodiments, the subject support device may be or included a meter sensor (such as a biological sensor) that continuously or intermittently senses a condition or collects data regarding a condition over time. A subject support device 12 may comprise, for example, but not limited to, an infusion pump or other infusion device for dispensing a controlled amount of an infusion medium to a subject, a meter for monitoring blood glucose or oxygen levels or other biological or medical condition over time, implantable or external sensors or meters for sensing or monitoring cardiac events, infectivity, hemodynamic pressure or other biological or medical event, a cardiac pacemaker, other electronic cardiac treatment device, or the like.

Representative and non-limiting examples of medical devices that may be employed as a subject support device according to certain embodiments of the invention are described in U.S. Pat. No. 6,641,533, titled "Handheld Personal Data Assistant (PDA) With A Medical Device And Method Of Using The Same" and U.S. patent application Ser. No. 10/033,724, titled "Infusion Device And Driving Mechanism For Same" (each of which are assigned to the assignee of the present invention and each of which is incorporated herein by reference in its entirety). Other suitable subject support devices may include, but are not limited to medical infusion pumps manufactured by Medtronic MiniMed and distributed under the model names Paradigm™ 512/712, Paradigm™ 511 and MiniMed 508. Representative examples of meter devices that may be employed as a subject support device include, but are not limited to, meters manufactured or otherwise provided by Medtronic-MiniMed (including Paradigm Link™ and BD Logic™), by Ascensia/Bayer (including DEX™-DEX2™ and Elite™-EliteXL™), or by LifeScan (including One-Touch™ Profile™, OneTouch™, Ultra™, OneTouch™ Basic™, Fast Take™, and SureSte™).

In further embodiments, a subject support device, such as an infusion pump as described above, may include an interface for communicating with one or more meters or sensors as described above and a memory for storing sensor or meter information. The interface may comprise an electrical port on each of the infusion pump and the sensor or meter through a hard-wire connector. Alternatively, the interface may comprise a wireless interface, such as an RF link, an optical link, a magnetic link or other suitable communication links. In this manner, an infusion pump may store information received from a sensor or meter over a period of time and, upon coupling the infusion pump to the network (as described herein), the stored information may be communicated to a system 16 server. Thus, the infusion pump may facilitate the collection and storage of information from one or more sensors and/or meters, and may communicate such information to the system 16 (along with stored pump setting or pump operation information) at a suitable time during a network communication session.

In the system 10 of FIG. 1, subject support devices 12 of multiple subjects or subjects may be connected in communication with respective subject-side computers 14. Each subject may have one or more subject support device 12 and at least one subject or subject-side computer 14. Each subject side computer may be connectable to a wide area network, such as the Internet. The system 10 also includes a medical data management system 16 connected to the wide area network and which is described in more detail below.

Depending upon the environment of use, embodiments may also include additional network devices, such as additional computers, connected in the system 10 through the wide area network. For example, as part of the data management system 16 (or as a separate element), one or more system personal, such as customer service operators and/or system administrators may be connected for communication in system 10, via a computer or other suitable network device 18. Such system personnel may be trusted individuals, employed by (or otherwise associated with) an entity administering the system 16, such that appropriate security and controls may be implemented for system personnel handling or having access to subject information. In some embodiments described below, system personnel may include physicians or other trained medical personnel that may have access to some or all subject information stored on the system 16, to provide assistance to subject-users and/or healthcare provider-users.

Alternatively or in addition, one or more service providers may be connected to the network for communication in the system 10, each via a respective computer or suitable network device 20. In the context of a health care system, a service provider may be, for example, but not limited to, a healthcare provider such as a doctor, authorized personnel at a doctor's office, a hospital, a laboratory, a treatment center, or the like. One or more payor entities also may be connected to the network for communication in the system 10, each via a respective computer or suitable network device 22. In the context of a health care system, the payor entity may be, for example, an insurance company, or the like.

The computers or other network devices 14, 18, 20 and 22 may each comprise a conventional personal computer or other suitable network-connectable communication device having data processing capabilities. For some embodiments with limited functions, the network device may comprise, but is not limited to a personal digital assistant (PDA), a mobile telephone, a pager, a dedicated medical communication device, or the like. Depending upon the embodiment and environment of use, the computers or other network devices 14, 18, 20 and 22 may include or otherwise be associated with a user input device (such as, but not limited to, a keyboard, mouse, touch screen, optical input device, or the like) and a display device (such as, but not limited to a cathode-ray tube monitor, an LCD display, an LED display, a plasma display or the like). For convenience and simplification of the present disclosure (and without limiting the present invention), embodiments are described herein with reference to the network devices 14, 18, 20 and 22 as computers.

The communication link 13 between each subject support device 12 and a subject-side computer 14 may be provided in any suitable manner including, but not limited to a direct or indirect hard wired connection (for example, through conventional communication ports on the device 12 and computer 14, such as a serial port, parallel port, RS-232 port, USB port or the like), a wireless connection (for example, radio-frequency or other magnetic or electro-magnetic link), an optical connection, a combination of the forgoing, or the like. For embodiments employing wireless or optical connections, the subject support device 12 and the subject-side computer 14, each include suitable wireless and/or optical transmitters and receivers for communication there between. In yet further embodiments, the subject support device 12 may be configured with suitable hardware and software to enable a direct connection of the subject support device 12 to the network (such as the Internet, LAN or extranet), as shown in FIG. 1, at reference number 25. Alternatively, or in addition, as shown at reference number 27 in FIG. 1, the subject support device may be connectable to the network (such as the Internet, LAN or extranet) through a separate network connection device 31 that provides some or all of the hardware and/or software for connection of the subject support device 12 to the network and communication on the network.

In one example embodiment, the communication link 13 employs a communication link device that interfaces with the subject support device 12 and connects to the subject-side computer 14 through a connector cable or the like. Example communication link devices include, but are not limited to, Com-Station™, ComLink™ or Paradigm Link™ devices. The connector cable may comprise, but is not limited to, a serial cable connector a BD-USB connector, or the like.

In a further embodiment, the communication link device may comprise a communication cradle (not shown) having a receptacle in which the subject support device 12 is configured to be set or installed for communication with the subject-side computer 14. The subject support device 12 may include electrical contacts, magnetic and/or optical connections that engage corresponding contacts or connections in or on the cradle, such that, upon setting the subject support device 12 in the cradle, a communication connection is made between the device 12 and the cradle. The cradle may, in turn, be connected by a wired or a wireless communication link to the subject-side computer 14.

The cradle allows a user to quickly and easily connect a subject support device to a subject-side computer 14, thus simplifying various activities and functions described herein. Thus, by setting the subject support device 12 in or on the cradle, an electronic communication link is created between the subject support device 12 and the subject-side computer 14. Examples of a communication cradle and other suitable communication links 13 are described and shown in published PCT Application No. PCT/US99/22993, titled "Communication Station And software For Interfacing With An Infusion Pump, Analyte Monitor, Analyte Meter, Or The Like" (which is owned by the Assignee of the present invention and which is incorporated herein by reference in its entirety).

With the communication link 13 coupling a subject-side computer 14 to one or more subject support devices 12, information including data, programs, updated software or the like may be transferred between the computer 14 and the device(s) 12. As described above, each subject-side computer 14 is also coupled for communication over a wide area network, such as the Internet, through a respective second communication link 15. The second communication link 15 may comprise any suitable communications connection and may employ, for example, a suitable Internet Service Provider (ISP) connection to the Internet and/or include a hard wired connection, a wireless connection, an optical connection, a combination of the forgoing, or the like. While not shown in the drawing, suitable modem, cable-modem, satellite, DSL or other system elements may be employed for connecting the subject-side computer 14 to the Internet. Similar communication links may be employed for connecting computers 18, 20 and 22 for communication over the Internet.

The medical data management system 16 is coupled for communication over the wide area network, such as the Internet, through one or more further communication links 17. The link(s) 17 may comprise any suitable communications connection and, for example, may employ one or more suitable Internet Service Provider (ISP) connection to the Internet and/or a hard wired connection, a wireless connection, an optical connection, a combination of the forgoing, or the like. While not shown in the drawing, suitable modem, cable-modem, satellite, DSL or other system elements for connecting the medical data management system 16 to the wide area network may be employed.

The medical data management system 16 comprises software that runs on at least one (or multiple) server(s) connected to the Internet. The system 10 may also include additional system software 19 residing on the subject-side computer 14, software 21 residing on the healthcare provider's computer 20, and software 23 residing on the payor entity computer 22 for interacting with the medical data management system 16 and providing functions described herein. The software 19, 21 and 23 may be stored in a hard-disc or other suitable computer readable storage device connected to the respective user computers 14, 20 or 22. The software 19, 21 and 23 may be supplied to the respective users by any suitable means, including, but not limited to computer readable discs delivered to the user by mail or other form of delivery, or by uploading such software to the user computers 14, 20 or 22 from the system 16, through an Internet connection, for example, during a registration procedure (as described below). Other system software (not shown) may be provided on the operator or administrator computer(s) 24, for providing similar functions and/or other functions for which the operator or administrator may be authorized to perform. The software for system 16 and the software residing on computers 14, 20 and 22 may be configured using any suitable standard or non-standard software coding techniques to provide functions described herein. Alternatively, or in addition, the functions of the management system 16 and/or the user computers 14, 20 and 22 described herein may be implemented in suitably configured hardware circuitry or combinations of hardware and software.

In general, the medical data management system 16 may be configured to provide any one or combination of functions to provide an expanded capability to treat individual subjects, as well as groups of subjects with similar medical conditions or other characteristics.

The Data Management System 16:

In the embodiment shown in FIG. 1, the data management system 16 comprises a group of interrelated software modules or layers that specialize in different tasks. The system software includes a device communication layer 24, a data parsing layer 26, a database layer 28, a reporting layer 30 and a user interface layer 32.

The device communication layer 24 is responsible for interfacing with at least one, and, in further embodiments, to a plurality of different types of subject support devices 12. In one embodiment, the device communication layer 24 may be configured to communicate with a single type of subject support device 12. However, in more comprehensive embodiments, the device communication layer 24 is configured to communicate with multiple different types of subject support devices 12, such as devices made from multiple different manufacturers, multiple different models from a particular manufacturer and/or multiple different devices that provide different functions (such as infusion functions, sensing functions, metering functions, or combinations thereof). As described in more detail below, by providing an ability to interface with multiple different types of subject support devices 12, the medical data management system 16 may be collect data from a significantly greater number of discrete sources. Such embodiments may provide expanded and improved data analysis capabilities by including a greater number of subjects and groups of subjects in statistical or other forms of analysis that can benefit from larger amounts of sample data and/or greater diversity in sample data, and, thereby, improve capabilities of determining appropriate treatment parameters, diagnostics, or the like.

The device communication layer 24 allows the medical data management system 16 to receive information from and transmit information to each subject-side computer 14 and/or each subject support device 12 in the system 10. Depending upon the embodiment and context of use, the type of information that may be communicated between the system 16 and a computer 14 or device 12 may include, but is not limited to, data, programs, updated software, education materials, warning messages, notifications, or the like. The device communication layer 24 may include suitable routines for detecting the type of subject support device 12 in communication with the system 16 and implementing appropriate communication protocols for that type of device 12. Alternatively or in addition, the subject support device 12 may communicate information in packets or other data arrangements, where the communication includes a preamble or other portion that includes device identification information for identifying the type of the subject support device. Alternatively, or in addition, the subject support device 12 and/or subject-side computer may include suitable user-operable interfaces for allowing a user to enter information, such as by selecting an optional icon or text or other device identifier, that corresponds to the type of subject support device used by that user. Such information may be communicated to the system 16, through the network connection. In yet further embodiments, the system 16 may detect the type of subject support device it is communicating with in the manner described above and then may send a message requiring the user to verify that the system 16 properly detected the type of subject support device being used by the user. For systems. 16 that are capable of communicating with multiple different types of subject support devices 12, the device communication layer 24 may be capable of implementing multiple different communication protocols and selects a protocol that is appropriate for the detected type of subject support device.

The data-parsing layer 26 is responsible for validating the integrity of device data received and for inputting it correctly into a database. A cyclic redundancy check CRC process for checking the integrity of the received data may be employed. Alternatively, or in addition, data may be received in packets or other data arrangements, where preambles or other portions of the data include device type identification information. Such preambles or other portions of the received data may further include device serial numbers or other identification information that may be used for validating the authenticity of the received information. In such embodiments, the system 16 may compare received identification information with pre-stored information to evaluate whether the received information is from a valid source.

The database layer 28 may include a centralized database repository that is responsible for warehousing and archiving stored data in an organized format for later access, and retrieval. The database layer 28 operates with one or more data storage device(s) 29 suitable for storing and providing access to data in the manner described herein. Such data storage device(s) 29 may comprise, for example, one or more hard discs, optical discs, tapes, digital libraries or other suitable digital or analog storage media and associated drive devices, drive arrays or the like.

Data may be stored and archived for various purposes, depending upon the embodiment and environment of use. As described below, information regarding specific subjects and patent support devices may be stored and archived and made available to those specific subjects, their authorized healthcare providers and/or authorized healthcare payor entities for analyzing the subject's condition. Also, certain information regarding groups of subjects or groups of subject support devices may be made available more generally for healthcare providers, subjects, personnel of the entity administering the system 16 or other entities, for analyzing group data or other forms of conglomerate data.

Embodiments of the database layer 28 and other components of the system 16 may employ suitable data security measures for securing personal medical information of subjects, while also allowing non-personal medical information to be more generally available for analysis. Embodiments may be configured for compliance with suitable government regulations, industry standards, policies or the like, including, but not limited to the Health Insurance Portability and Accountability Act of 1996 (HIPAA).

For example, embodiments may employ suitable registration procedures, user identification and password verification procedures before allowing access to sensitive or personalized information (information with individual identifiers) and/or suitable encryption procedures for storing such information in the database storage device(s) 29 and/or communicating such information. Alternatively, or in addition, the database storage device(s) 29 may include at least two separated sections (which may be implemented in one storage device with separate data storage areas or in multiple, separated storage devices), including a first section for storing information with individual identifiers and a second section for storing information free of individual identifiers. Thus, for example, the first section(s) may store specific subject information with individual identifiers that identify each individual subject, for access by the subject or other authorized personnel (such as the subject's authorized healthcare provider or payor entity). The second section(s) may store information, such as non-personalized information and/or group or conglomerate information, but without individual subject identifiers (de-identified information), for access by authorized or by other personnel for analysis, research or other suitable purposes. Individual identifiers may include, for example, a subject's name, address, workplace, or other information that may be designated as an individual identifier in a regulation, standard or policy for which the system may be configured to meet.

In one example, the first section(s) of the database(s) 29 may include all of the same information in the second section(s) of the database(s) 29 but with individual identifiers. For example, the second section(s) of the database(s) 29 may contain a stripped version or copy of the information in the first section(s) of the database(s) 29 (stripped of personal identifiers). Thus, the first section(s) of the database(s) 29 may be accessed for performing secure functions as described herein. The second section(s) may be accessed for performing functions that involve non-personalized information, such as evaluation of group trends, evaluating particular treatments and results without subject information, or the like. The database layer 28 may include one or more suitable routines for reconciling data in the first and second database sections, such that each section includes the same versions of any common (stripped) information.

Alternatively, or in addition, the first section(s) of the database(s) 29 may include personal information for each subject-user, where each subject-user's personal information is associated with a corresponding storage location in the second section(s) of the database(s) 29 (or corresponding information in the second section(s) of the database(s) 29). Such correspondence may be made by associating an address or other identifier for information or locations in the corresponding second section(s) with the information or locations in the first section(s). Such address or other identifiers may be stored with (or in association with) the information in the first section(s), and may be retrieved with (or in association with) retrieval of personal information from the first section(s) to provide access to corresponding non-personal information in the second section(s) of the database(s).

The database layer 28 may be configured to limit access of each user to types of information pre-authorized for that user. For example, a subject may be allowed access to his or her individual medical information (with individual identifiers) stored by the database layer 28, but not allowed access to other subject's individual medical information (with individual identifiers). Similarly, a subject's authorized healthcare provider or payor entity may be provided access to some or all of the subject's individual medical information (with individual identifiers) stored by the database layer 28, but not allowed access to another individual's personal information. Also, an operator or administrator-user (on computer 24) may be provided access to some or all subject information, depending upon the role of the operator or administrator. On the other hand, a subject, healthcare provider, operator, administrator or other entity, may be authorized to access general information of un-identified individuals, groups or conglomerates (without individual identifiers) stored by the database layer 28.

The reporting layer 30 may include a report wizard program that pulls data from selected locations in the database 28 and generates report information from the desired parameters of interest. The reporting layer 30 may be configured to generate multiple different types of reports, each having different information and/or showing information in different formats (arrangements or styles), where the type of report may be selectable by the user. A plurality of pre-set types of report (with pre-defined types of content and format) may be available and selectable by a user. At least some of the pre-set types of reports may be common, industry standard report types with which many healthcare providers should be familiar.

Alternatively, or in addition, the report wizard may allow a user to design a custom type of report. For example, the report wizard may allow a user to define and input parameters (such as parameters specifying the type of content data, the time period of such data, the format of the report, or the like) and may select data from the database and arrange the data in a printable or displayable arrangement, based on the user-defined parameters. In further embodiments, the report wizard may interface with or provide data for use by other programs that may be available to users, such as common report generating, formatting or statistical analysis programs such as, but not limited to, EXCEL™, or the like. In this manner, users may import data from the system 16 into further reporting tools familiar to the user. The reporting layer 30 may generate reports in displayable form to allow a user to view reports on a standard display device, printable form to allow a user to print reports on standard printers, or other suitable forms for access by a user. Embodiments may operate with conventional file format schemes for simplifying storing, printing and transmitting functions, including, but not limited to PDF, JPEG, or the like. In certain embodiments in which security measures are implemented, for example, to meet government regulations, industry standards or policies that restrict communication of subject's personal information, some or all reports may be generated in a form (or with suitable software controls) to inhibit printing, or electronic transfer (such as a non-printable and/or non-capable format). In yet further embodiments, the system 16 may allow a user generating a report to designate the report as non-printable and/or non-transferable, whereby the system 16 will provide the report in a form that inhibits printing and/or electronic transfer.

Data analysis and presentations of the reported information may be employed to develop and support diagnostic and therapeutic parameters. Where information on the report relates to an individual subject, the diagnostic and therapeutic parameters may be used to assess the health status and relative well being of that subject, as well as to develop or modify treatment for the subject. Where information on the report relates to groups of subjects or conglomerates of data, the diagnostic and therapeutic parameters may be used to assess the health status and relative well being of groups of subjects with similar medical conditions, such as, but not limited to, diabetic subjects, cardiac subjects, diabetic subjects having a particular type of diabetes or cardiac condition, subjects of a particular age, sex or other demographic group, combinations thereof, or the like.

The user interface layer 32 supports interactions with the end user, for example, for user login and data access, software navigation, user data input, user selection of desired report types and the display of selected information. As described in more detail below, users may be subjects, healthcare providers, healthcare payer entities, system operators or administrators, or the like, depending upon the service being provided by the system and depending upon the invention embodiment. More comprehensive embodiments are capable of interacting with some or all of the above-noted types of users, wherein different types of users have access to different services or data or different levels of services or data.

In an example embodiment, the user interface layer 32 provides one or more websites accessible by users on the Internet. The user interface layer may include or operate with at least one (or multiple) suitable network server(s) to provide the website(s) over the Internet and to allow access, world-wide, from Internet-connected computers using standard Internet browser software. The website(s) may be accessed by various types of users, including subjects, healthcare providers, payor entities, pharmaceutical partners or other sources of pharmaceuticals or medical equipment, and/or support personnel or other personnel running the system 16, depending upon the embodiment of use.

A subject may access a website to perform one or more of a variety of tasks, such as accessing general information made available on the website to all subjects or groups of subjects, to access specific information or to generate reports regarding that subject's medical condition or that subject's medical device(s) 12, to download data or other information from that subject's support device(s) 12 to the system 16, to upload data, programs, program updates or other information from the system 16 to the subject's support device(s) 12, to manually enter information into the system 16, to engage in a remote consultation exchange with a healthcare provider, or to modify the subject's custom settings.

By coupling a subject support device to a subject-side computer and by accessing a system 16 website through the subject-side computer, various different communication tasks may be performed with the subject support device. For example, preferred or updated control parameters or control settings may be communicated to the subject-side computer or the subject support device. In an example in which the subject support device is an infusion pump, various pump settings may be communicated to the subject-side computer or infusion pump, for setting pump parameters such as, but not limited to, basal rate, bolus amount, infusion start or stop times or dates, or the like. Alternatively, or in addition, new programs or program upgrades, or updated data may be communicated over the Internet to the subject-side computer or the subject support device. In this manner, preferred software, data, control settings or parameters may be communicated from a centralized system 16 to each subject-side computer and subject support device (or selected subject-side computers and subject support devices) in the system 10.

Also, by coupling a subject support device 12 to a subject-side computer 14 and by coupling the subject-side computer 14 in communication with the system 16 over the Internet, the medical data management system 16 may retrieve and collect data from the subject support device 12 and/or the subject-side computer 14. Such data may comprise data relating to the operation of the subject support device 12 over a period of time. For example, in embodiments in which the subject support device 12 is an infusion pump, the system 16 may collect data relating to the amount of media infused into the subject over time, bolus amounts and times, basal rates and time periods at which those rates were administered, meter or sensor data and times or dates at which the data was obtained, or the like. In addition, the subject may enter further information manually, for example, through the subject-side computer 14 or through a manual interface on the subject support device 12. Such additional information may include, for example, information relating to a subject's activity, such as dietary information, eating times and amounts, exercise times and amounts, or the like.

In systems 10 embodiments that include many subject support devices 12 of many different subjects, the medical data management system 16 may collect information from each of those subject support devices. The evaluation of such group or conglomerate information from many different subjects and/or many different subject support devices can provide valuable information about treatment results, trends and practices. Based on such treatment results, trends and practices, a subject or a healthcare provider may be able to develop or modify a preferred treatment for an individual subject. In addition, healthcare providers, payor entities and others may be able to analyze such treatment results, trends and practices to develop better practices for future treatments of individuals or groups of subjects with similar conditions.

A healthcare provider, using a computer or other network device 20, may access a website of the medical data management system 16 to perform a variety of tasks. Such tasks may include accessing general information made available on the website to all healthcare providers or groups of healthcare providers, to access specific information or to generate reports regarding a subject's medical condition or a subject's medical device(s) 12, to upload data or other information from a subject's support device(s) 12, to download data, programs, program updates or other information to the subject's support device(s) 12, to access and/or approve of treatment recommendations or to provide payment requests, such as invoices to a payor entity. For example, such tasks may include accessing data representing aggregate subject information for a plurality of subject-user's in the system 10, for example, to evaluate possible treatment trends, determine quality of care guidelines or the like. Such tasks may further include issuing electronic treatment plans or recommendations, electronic prescriptions or the like.

A payor entity, using a computer or other network device 22, may access a website of the medical data management system 16 to perform a variety of tasks associated with the payor entity. Such tasks may include accessing general information made available on the website to all payor entities or groups of payor entities, receiving payment requests from healthcare providers, accessing specific information or generating reports regarding a subject's medical condition or a subject's medical device(s) 12, accessing data representing aggregate subject information for a plurality of subject-user's in the system 10, for example, to evaluate possible treatment trends, determine quality of care guidelines, or providing responses to healthcare providers' payment requests. For example, a payor entity may be able to access subject information for at least some subjects (for example, subjects for which a healthcare provider has submitted a payment request) to evaluate changes in a subjects' conditions or healthcare outcomes, for example, in response to a treatment implemented by the subject's healthcare provider. Because some payor entities may be more interested in certain tests or subject responses, while other payor entities may be more interested in other tests or responses, the system 16 preferably allows a payor entity to access various types of information regarding subjects. Such information may be prepared by the system 16 (report wizard) in a report to the payor entity. Each payor entity may register a preferred report format (or specify information to include in a report), so that the system 16 generates an appropriate report suited for each payor entity. Such report format information may be registered during a registration process (described below) or as part of another suitable routine performed by the system 16 for obtaining information from the payor entity.

A system operator or administrator (or other system personnel, such as trained physicians or other trained medical personnel working for or with the entity operating the system), using a computer or other network device 24, may access the medical data management system 16; for example, to assist a user in a customer-help transaction, to access data for evaluation, for servicing the system including adding or modifying website content, or for other suitable activities. In an example embodiment, a physician or other trained medical personnel associated with the entity operating the system 16 may be provided with access to certain subject information for analysis. In yet further embodiments, such physicians or other trained personnel may operate a help desk environment, that allows users to contact help desk personnel for assistance with operation of system components and/or evaluation of subject or medical device information. Based on an analysis of such information, the system 16 physician or other medical personnel may provide treatment recommendations to a subject-user (or group of subject-users) or to the subject user's (or group's) designated healthcare provider(s). In a further example embodiment, the system 16 may store such treatment recommendations for access by a subject-user (or group of subject-users) and/or designated healthcare provider-user through a system website. In yet further example embodiments, the system 16 may require review and approval by the subject-user's designated healthcare provider of any treatment recommendations issued by a system 16 personnel, before such treatment recommendations are provided to the subject-user.

Figure 2:
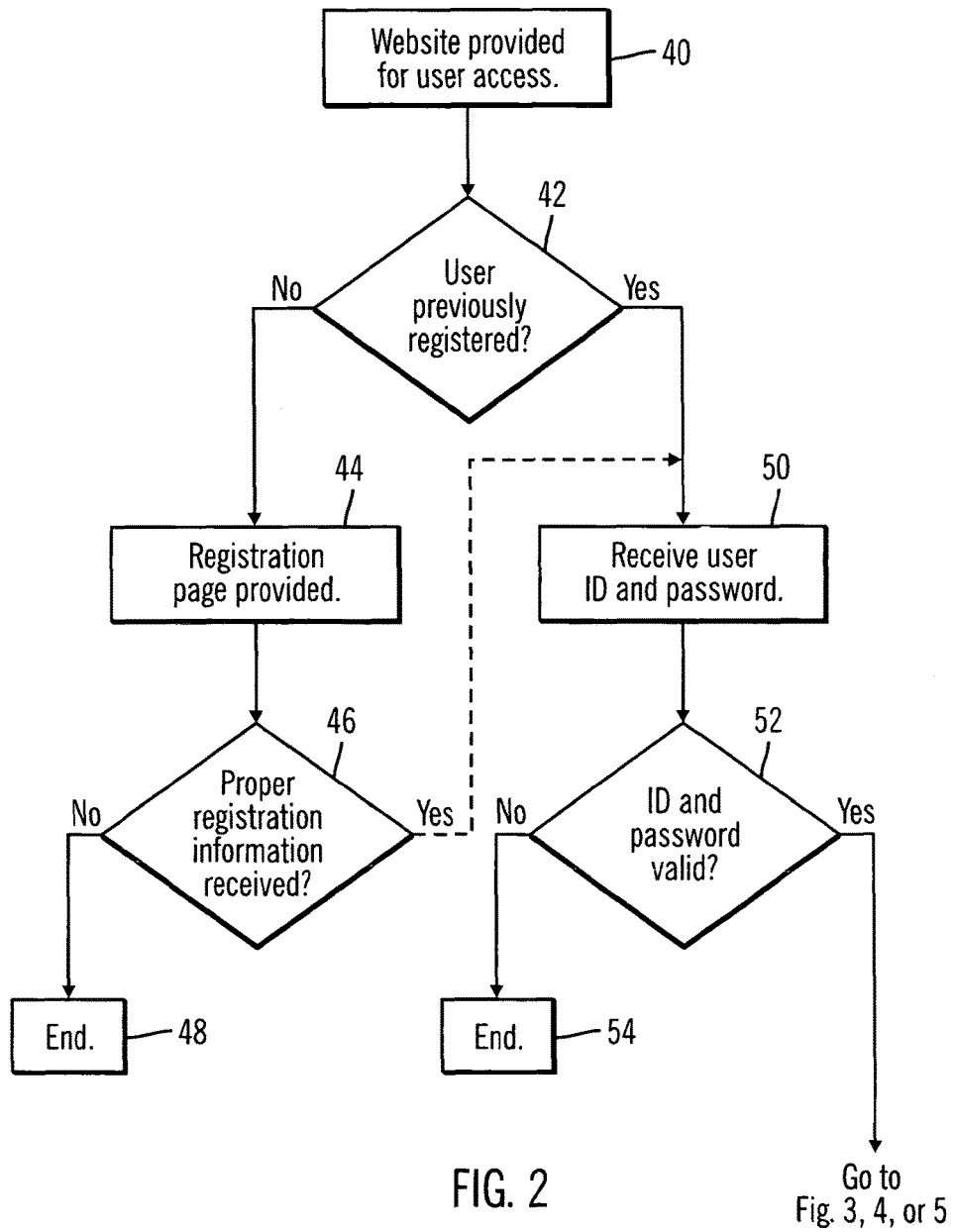
FIG. 2 is a generalized flow chart showing an example user-access process.

User Registration Processes:

FIG. 2 shows a flow chart of an example process of providing a user with access to information and services available from the medical data management system 16 through a system 16 website. In box 40 of FIG. 2, the medical data management system 16 provides an Internet website for access by a user. The website may be provided on one or more host servers, as described above, using conventional (or suitable non-conventional) website hosting techniques and suitable security measures to provide secure, controlled access to website locations, links and data. The website may include a plurality of website pages (or locations), accessible from selectable icons (or links) from other pages (or locations) on the site, in accordance with well known principles of website design and operation.

A user may access the website by launching a commonly available Internet Web Browser program on a personal computer, such as a subject-side computer 14 (for a subject-user), a healthcare provider computer 20 (for a healthcare provider-user) or a payor entity user 22 (for a payor-user). The user may connect to the Web through a common Internet Service Provider (for example, but not limited to, Earthlink, SBC/Yahoo, America Online, etc.). The user enters the address for a system 16 web site into the Web Browser program and accesses the website opening page to begin a communication session with the system 16.

The opening page (or another location on the website) may include a message or other indicia to prompt the user to enter information indicating whether or not the user has previously registered in the system 16. The system 16 is configured to receive such information from the user and, based on that information, to make an initial determination of whether or not the user has previously registered, as represented by box 42. If not, the user may be provided with a registration page, in which the user is prompted to enter registration information, as represented by box 44. As part of the registration process, or as part of other communication processes with the system 16, the user may be prompted by the system 16, or otherwise provided access (for example, by link, pop-up window, directed page or other location on the system 16 website), to review terms or conditions of acceptance, including, but not limited to, privacy terms and conditions. The system 16 also may require the user to acknowledge acceptance of terms or conditions, for example, by selecting an acceptance icon or entering other information in the user's computer or subject support device, for communication to the system 16 over the network connection. Similarly, the system 16 may require the user to verify place of residence, citizenship or other information that may be useful or legally required for receiving or providing medical assistance in certain countries or geographical regions.

From the registration page, a user may be prompted to enter user-specific information. The type of information requested on the registration page will depend upon the type of user registering on the system 16. At least some of the information requested from subject-users may be different than information requested from healthcare provider-users or from payor-users. Registration information regarding a subject-user may include contact information (such as user identification, postal address, telephone number, email address and the like) and medical information (such as the subject-user's gender, age, medical condition, type of diabetes, or the like). Registration information also may include security information for forming security questions used by the system 16 during subsequent user interactions with the system 16.

The system 16 is configured to receive registration information entered by the user from the registration page (or other suitable location on the website) and to determine if the information is valid or otherwise proper, as represented by box 46 in FIG. 2. If the system 16 determines that it did not receive proper registration information, the system 16 may provide the user with a message or other indicia indicating the failure to receive registration information and may either return the user to the registration page (box 44) or end the session (box 48). If the system 16 determines that registration information received from a user appears proper, the system 16 allows the user to proceed with the session, as represented by the "Y" arm extending from box 46.

As part of the registration process, the system 16 may upload software routines or programs, data or combinations thereof to the subject-side computer 14, for controlling the subject side computer to provide functions described herein. Also as part of the initial registration process, a new user-registrant may be required to exit the system website and re-access the system (to re-enter the user name and password) before being allowed to conduct further activities with the system. For additional security, the user may be required to select a new password upon the user's first re-access of the system 16 website after the user's initial registration.

If the user has previously registered, the medical data management system may provide the user with a message or other indicia to prompt the user to enter the user's previously registered identification information, such as a unique user name or identification code, and a password, as represented by box 50. The system 16 may include suitable security features for allowing the user to communicate the password in a secure manner. Such security features may include suitable encryption techniques, or the like. Depending upon the type of security employed, the system 16 and the user's computer may communicate encryption keys or other security information, for example, during a handshake procedure (or other suitable time in the session).

The system 16 is configured to receive the user identification information and password and to verify the information and password, to determine if the user information and password appear valid, as represented by box 52 in FIG. 2. Verification of the information and password may be carried out by the system 16, in any suitable manner, including, but not limited to, comparing the received password with a pre-stored password corresponding to the user identification information received from the user. Thus, for example, the database layer 28 in system 16 may include or employ a secure storage of a table (or other format) of user identification information with corresponding passwords, to allow the system to perform a table look-up (or other suitable retrieval) of a password that corresponds to user identification information received from a given user.

If the password received from that user does not sufficiently match the password retrieved from the table (or other data format), then the system 16 determines that the received user information and password do not appear to be valid. In that event, the system 16 may provide the user with a message or other indicia indicating the failure to receive proper user identification information and/or a proper user password, and may either return the user to the prompt to enter such information (box 50) or end the session (box 54).

On the other hand, if the password received from that user sufficiently matches the password retrieved from the table (or other data format), then the system determines that the received user information and password appear valid and allows the user to proceed with the session, as represented by the "Y" arm extending from box 52. In that event, the system 16 may provide the user with access to one or more selectable resources, such as items of information or services. For example, the user may be provided with a page, menu or other data format that provides a plurality of user-selectable identifiers, icons or other indicia representing information items and/or services available to that user from the system 16.

The system 16 may provide access to different optional resources or activities (including accessing different information items and services) to different users and to different types or groups of users, such that each user may have a customized experience and/or each type or group of user (e.g., all subject-users, diabetes subject-users, cardio subject-users, healthcare provider-user or payor-user, or the like) may have a different set of information items or services available on the system. The system 16 may include or employ one or more suitable resource provisioning program or system for allocating appropriate resources to each user or type of user, based on a pre-defined authorization plan. Resource provisioning systems are well known in connection with provisioning of electronic office resources (email, software programs under license, sensitive data, etc.) in an office environment, for example, in a local area network LAN for an office, company or firm. In one example embodiment, such resource provisioning systems is adapted to control access to medical information and services on the system 16, based on the type of user and/or the identity of the user.

Subject-User Processes:

If the user is a subject-user, then upon entering successful verification of the user's identification information and password, the subject may be provided access to secure, personalized information stored on the system 16. For example, the subject-user may be provided access to a secure, personalized website location assigned to the subject, as represented by box 60 in FIG. 3. The personalized website location may provide a personalized home screen to the subject, including selectable icons or menu items for selecting optional activities, including, for example, an option to download device data from a subject support device 12 to the system 16, manually enter additional data into the system 16, modify the subject's custom settings, and/or view and print reports. Reports may include data specific to the subject's condition, including but not limited to data obtained from the subject's subject support device(s) 12, data manually entered by the subject or healthcare provider, data from medical libraries or other networked therapy management systems, or the like. Where the reports include subject-specific information and subject identification information, the reports may be generated from some or all subject data stored in a secure storage area employed by the database layer 28. In addition, suitable security measures may be implemented in the communication of the reports over the Internet. Such security measures may include, but are not limited to, encryption techniques, or the like.

Figure 3:
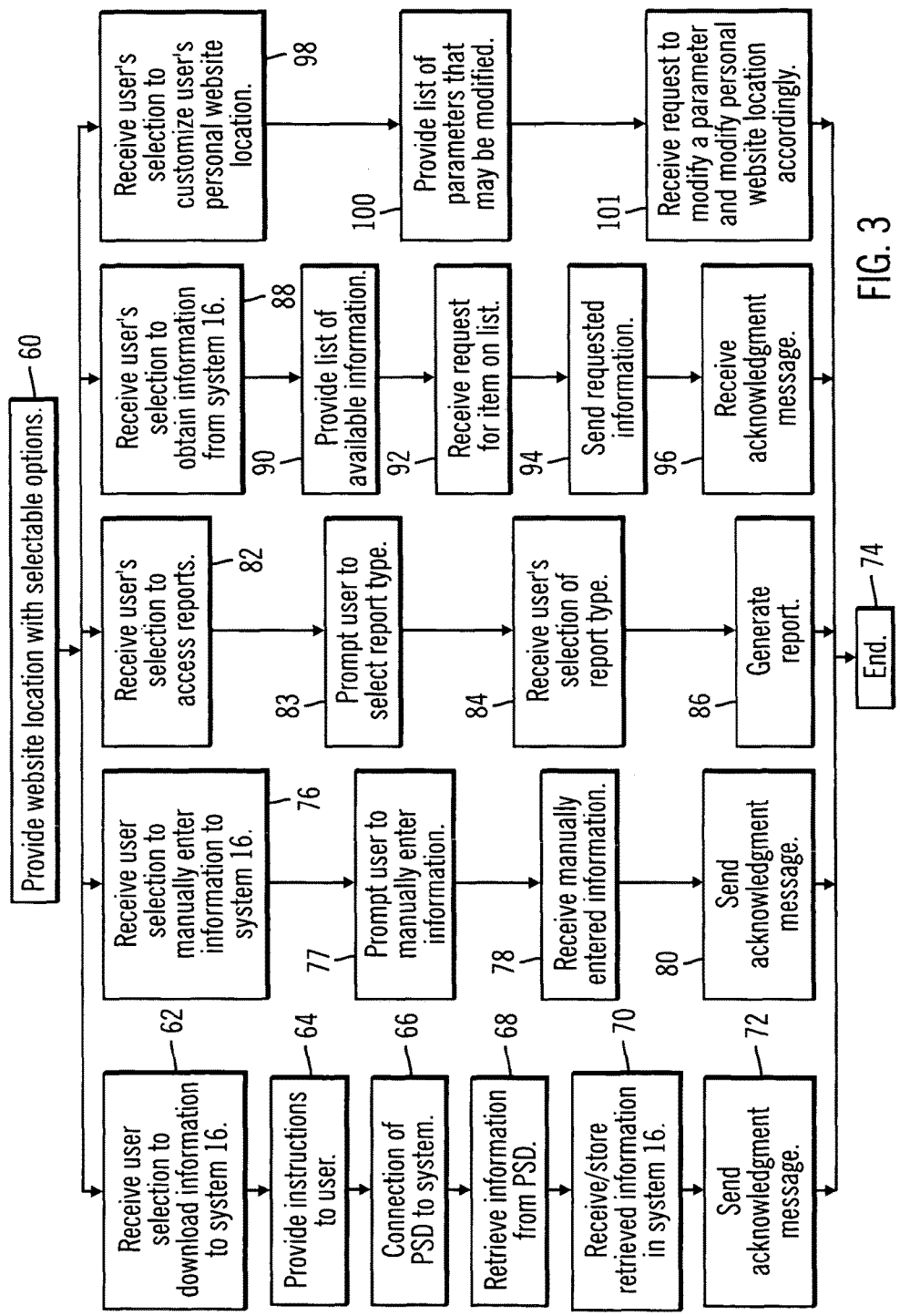
FIG. 3 is a generalized flow chart showing examples of optional processes for subject-users.

FIG. 3 is a flow-chart of example optional processes that may be performed with a subject-user. In FIG. 3, upon providing the subject-user with a plurality of user-selectable options for resources on the user's personalized website location (box 60), the user may select an option to download (send) device data to the medical data management system 16. If the system 16 receives a subject-user's request to download device data to the system (box 62), the system 16 may provide the user with step by step instructions on how to download data from the subject's subject support device. For example, the system 16 may have a plurality of different stored instruction sets for instructing users how to download data from different types of subject support devices, where each instruction set relates to a particular type of subject support device (e.g., pump, sensor, meter, of the like), a particular manufacturer's version of a type of subject support device, or the like. Registration information received from the subject user during registration (box 46 in FIG. 2) may include information regarding the type of subject support device(s) 12 used by the subject. The system 16 employs that information to select the stored instruction set(s) associated with the particular subject's support device(s) 12 for display to the subject-user, as reprinted by box 64.

The instructions may include details regarding how to couple the subject's support device(s) 12 for communication with the medical data management system 16. For example, the instructions may include details for connecting the subject's device(s) to the subject-side computer 14. As shown in box 66 of FIG. 3, one or more subject support devices 12 may be electronically connected to the subject side computer 14. The subject-user may make the electrical connection, for example, employing a cradle type communication device as described above, or other suitable connector. Following on-screen prompts, the subject-user may input commands to cause the subject-side computer 14 to retrieve device history information from the subject support device(s) 12. Alternatively, or in addition, such commands may be communicated from the medical data management system 16 to the subject support device(s) 12, through the subject-side computer 14.

In an example embodiment, software 19 residing on the subject-side computer 14 allows the computer 14 to communicate with the subject support device(s) 12 and retrieve and, at least temporarily, store device history information there from, as represented by box 68 in FIG. 3. Device history information may include any suitable information regarding the history of operation of the subject-support device. Such information may differ for different types of subject support devices. For example, in embodiments in which the subject support device 12 is an insulin infusion device (such as an insulin pump) for a diabetes subject, device history information may include, but is not limited to, bolus delivery amounts and times, basal rate amount and time, reservoir capacity, battery life, maximum settings for basal or bolus amounts or times, temporary basal rates, bolus type setting, remote bolus delivery amounts and options, bolus wizard setting and types, warning types and amounts, alarm clock options, remote meter options, or the like. In embodiments in which the subject support device is an electronic insulin infusion pump, device history information may include insulin delivery data, device settings, log history, blood glucose data (manually entered or captured by sensors or meters. In embodiments in which the subject support device is discrete blood glucose meter, device history information may include blood glucose readings and/or other events or activities of the user that may effect the user's medical condition. In embodiments in which the subject support device is a continuous glucose monitoring sensor, device history information may include continuous glucose readings, sensor settings and sensor status information.

As represented by box 70 in FIG. 3, information retrieved from the subject support device(s) 12 is communicated to and received by the medical data management system 16. For example, software 19 residing on the subject-side computer 14 may control the subject-side computer 14 to forward information retrieved from the subject support device(s) 12 to the system 16, either as it is retrieved from the subject support device(s) 12 or after retrieving and at least temporarily storing such information. Such information may be communicated through the Internet, for example, as part of the Internet communication session established between the subject-side computer 14 and the medical data management system 16.

In this manner, the system 16 may receive information that had been collected and stored by the subject support device(s) 12. Thus, a subject support device 12 may be a type which continuously or intermittently senses a condition (a medical condition, a condition of the support device itself, or environmental condition associated with a subject) and collects sensed data over time. The collected sensed data may be communicated to the system 16 (and/or to the subject-side computer 14), when the subject support device 12 is connected to the system (through the subject-side computer 14). As a result, the system 16 may receive and store information relating to a continuous or intermittent sensor data from a subject support device 12, even though the system 16 need not be continuously connected for communication with the subject support device 12.

As represented by box 72, the medical data management system 16 may provide an acknowledgment message back to the subject-side computer, for example, upon a successful receipt of information to a system 16 server and/or storage of the information in a database section established for the subject-user. The subject-user may be prompted again to select an activity or resource available on the system 16, for example, by being returned to the subject-user's personalized user website location (box 60). Alternatively, or in addition, if no further activities are to be performed with the system 16, the communication session may be ended, as represented by box 74.

Other activities or resources available to the subject-user on the system 16 may include an option for manually entering information to the medical data management system 16. For example, from the subject-user's personalized website location (box 60 in FIG. 3), the subject-user may select an option to manually enter additional information into the system 16. As represented by box 76 in FIG. 3, the medical data management system 16 may receive a user's selection of an option to manually enter information.

The system 16 may receive manually entered information from the subject-user in any suitable manner, as represented by box 78. For example, as represented by box 77, the system 16 may prompt the user with queries or other messages, indicating the type of information that the user may manually enter. As noted above, such information (and prompts) may depend upon the particular medical condition of subject and/or the type of subject support device(s) used by the subject, which the system 16 may determine during the subject-user's registration process. For example, to receive a user's manually entered information, the system 16 may communicate an electronic form to the subject-side computer 14, where the electronic form has queries and/or defined locations for inputting specific information to the subject-side computer 14 for completion by the subject and for returning to the system 16, when completed. Alternatively, such a form may have been previously stored on the subject-side computer, for example, as part of the loading of the subject-side portion of the system 10 software into the subject-side computer 14).

A subject-user may manually enter information, for example, using standard (or non-standard) user interface devices on the subject-side computer 14, including, but not limited to, a keyboard, a mouse, a touch screen, an optical input device, or the like. Alternatively, or in addition, the subject support device(s) 12 may include one or more user interfaces (buttons, keys, touch screen, or the like) for a subject-user to manually enter information. In further embodiments, other external devices (not shown) may be connected to the subject-side computer 14, for allowing a subject-user to manually input information.

Such manually entered information may be stored with (or associated with) registration and/or retrieved information regarding the subject and the subject's support device(s). The type of information that may be entered manually may depend upon a variety of factors, including the particular medical condition of the subject, the type of subject support device(s) used by the subject, requirements or instructions of the subject's healthcare provider, or the like. Such manually entered information may include information that is in addition to (for example, not available from) information that may be received from the subject's support device(s) 12. Thus, for example, a diabetes subject may manually enter additional information regarding the subject's dietary intake including, but not limited to eating times, types of foods consumed, calories consumed, sugar content of consumed foods, carbohydrate content of consumed foods, content or concentrations of other elements in consumed foods, or the like. Alternatively, or in addition, a diabetes subject-user may manually enter non-dietary information, such as information regarding sleeping times or periods, exercise times or periods, exercise amounts, urine keytones (such as HbA1c information), infusion set changes, other user activities or events that affect the user's medical condition including exercise periods of time and level of strain, sleep times and periods, ingestion of medicines or other non-food materials, or the like.

As represented by box 80, the medical data management system 16 may provide an acknowledgment message back to the subject-side computer, for example, upon a successful receipt of manually entered information to a system 16 server and/or storage of the manually entered information in a database section established for the subject-user. The subject-user may be prompted again to select an activity or resource available on the system 16, for example, by being returned to the subject-user's personalized user website location (box 60). Alternatively, or in addition, if no further activities are to be performed with the system 16, the communication session may be ended, as represented by box 74.

Another activity or resource available to the subject-user on the medical data management system 16 may include an option for requesting reports. For example, from the subject-user's personalized website location (box 60 in FIG. 3), the subject-user may select an option to generate, view or print reports containing information stored by the system 16. As represented by box 82 in FIG. 3, the medical data management system 16 may receive a user's selection of an option to view or print reports. In response, as represented by box 83, the system 16 may prompt the user to select a type of report (for example, type of report contents, format and/or style), such as by providing the user with a table, list, menu or other suitable arrangement of a plurality of optional reports from which the user may select a desired report.

Thus, information previously received by the system 16, for example, from the subject's support device(s) 12 (such as shown in box 70) and/or from manual entry by the subject (such as shown in box 78), may be included in one or more reports. The system 16 may have a plurality of pre-defined report types, for displaying different reported information and/or in various manners. For example, different available reports (report types) may include respectively different data and/or different data formats, such as one or more bar graphs, x-y coordinate graphs, pie charts, tables, scatter charts, stacked bar charts, interactive data presentations, or the like. In further embodiments, the subject-user may be provided with options for generating a report, for example, by customizing a pre-existing report type or by creating an original type of report with user-defined types of data content and/or user-defined presentation format. Thus, a subject-user may design a report to include certain information specified by the subject-user and/or to present certain information in a particular format specified by the user.

A subject-user may select from a plurality of available reports and/or options for generating a report by defusing data content and/or format parameters and, as represented by box 84, the system 16 may receive the subject-user's selection (and content or format parameters). In one embodiment, a subject-user may receive a report and/or parameters for generating a report from the subject-user's designated healthcare provider. The report and/or parameters may be stored on the system 16 database and accessible by the subject-user, for example, as part of a process for receiving information from the system 16 as described below with respect to boxes 88-96 in FIG. 3. In that manner, a subject-user's healthcare provider may select an existing type of report or design a report that the healthcare provider believes would be helpful to that subject (for example, based on the healthcare provider's assessment of that subject's medical condition, habits, ability to understand reports, or other personal information that may be available to the particular healthcare provider treating that subject).

Based on the subject-user's selected report or defined report parameters, the system 16 generates a suitable report, as represented by box 86 and forwards the report to the subject-side computer 14, for example, over the Internet connection. Alternatively, or in addition, the system 16 may forward data or other information to the subject-side computer 14 over the Internet connection, such that system software 19 residing on the subject-side computer 14 may generate the report with that data or other information. The system 16 may be configured to implement suitable security measures for reports or information communicated to the subject-side computer 14, over the Internet, such as, but not limited to, suitable encryption techniques, authentication techniques, password protection, or the like.

Generated reports may be displayed on a screen of a display device associated with the subject-side computer 14. Alternatively, or in addition, a subject-user may store reports on a storage device (not shown) associated with the subject-side computer 14 for later viewing or print reports on a printer (not shown) associated with the subject-side computer 14 for a hard copy representation of the same displayed information. If desired, the subject-user may send copies of one or more reports, data or other information to their healthcare provider or bring printed report copies to their next scheduled office visit. In one example embodiment, the system 16 website or the system software 19 residing on the subject-side computer 14 may provide an option to the subject-user to email a generated report, data or other information to the subject-user's healthcare provider.

Following the generation of a report, the subject-user may be prompted again to select an optional activity or resource available on the system 16, for example, by being returned to the subject-user's personalized user website location (box 60). Alternatively, or in addition, if no further activities are to be performed with the system 16, the communication session may be ended, as represented by box 74.

Further optional activities or resources may be available to the subject-user on the medical data management system 16. For example, from the subject-user's personalized website location (box 60 in FIG. 3), the subject-user may select an option to receive data, software, software updates, treatment recommendations or other information from the system 16 on the subject's support device(s) 12. If the system 16 receives a request from a subject-user to receive data, software, software updates, treatment recommendations or other information (box 88 in FIG. 3), the system 16 may provide the subject-user with a list or other arrangement of multiple selectable icons or other indicia representing available data, software, software updates or other information available to the user (box 90 in FIG. 3). When a subject-user selects one or more of the icons or other indicia, the system 16 may receive the subject-user's request for data, software, software updates or other information to be sent to the subject-side computer 14 and/or a subject support device 12 connected thereto (box 92) and transmits the requested information to the subject-side computer 14 and/or the subject support device 12 (box 94).

Alternatively, or in addition, some or all of the data, software, software updates treatment recommendations or other information available to the subject-user may be automatically communicated to the subject-side computer 14 and/or a subject support device 12 connected thereto, upon the system 16 receiving a general request to obtain such information (box 88) and without the need for the user to receive a list and individually select information items from the list (boxes 90 and 92). Alternatively or in addition, the system 16 and/or the system software 19 residing on the subject-side computer 14 may be configured to provide the subject-user with data, software, software updates, treatment recommendations or other information automatically during a communication session with the system 16 (without requiring the user to select an option to upload such information in box 88).

As represented by box 96, the system software 19 residing on the subject-side computer 14 may cause the subject-side computer to send an acknowledgment message back to the medical data management system 16, and the system 16 may receive such an acknowledgment message over the Internet, for example, upon a successful receipt by the computer 14 of information from the system 16. The subject-user may be prompted again to select an activity or resource available on the system 16, for example, by being returned to the subject-user's personalized user website location (box 60). Alternatively, or in addition, if no further activities are to be performed with the system 16, the communication session may be ended, as represented by box 74.

By providing the system 16 with the capability to forward data, software, software updates, treatment recommendations or other information to subject-users throughout the system 10, each active subject-user may be provided with the most updated versions of software for controlling the subject's support device(s) 12, the most updated versions of the system software 19 residing on the subject-side computer 14 and/or the most updated general or subject-specific information. Such general or subject-specific information may include, but is not limited to warning messages, alerts, new study results, or other information relating to the subject's support device(s) 12 and/or medical condition. Alternatively, or in addition, such information may include courses or classes that provide instructions to the user, for improving health care, for improving operations of the subject support device, or the like. In an Internet environment, such courses or classes may include bi-directional, interactive communications between the user and the system 16 (or system software running on the user's computer), for example, to provide the user with questions, receive user's answers and to modify or direct the course, based on the user's answers. In this manner, the medical data management system may be employed to help manage and educate subject-users on the system 10, to provide a more comprehensive and consistent usage of the most appropriate and advanced products and services available to the subject-users.

For example, data received from a subject and/or a subject's support device 12 may be analyzed by suitable medical personnel from the subject's healthcare provider or from an entity administering the system 16. Based on that analysis, the medical personnel may cause the system 16 to send new software, software update(s), data and/or warning messages, instructions, on-line classes, tips for improved health or for better usage of the subject's support device 12, or the like. Thus, for example, a medical practitioner may analyze data received from a subject's support device 12 and/or a subject's computer 14 and determine that the user is not receiving enough insulin after the subject exercises. Based on that analysis, the medical practitioner may cause the system 16 to communicate a message to the subject's computer 14, instructing the subject to adjust the subject's insulin delivery program. In addition, the medical practitioner may cause the system 16 to communicate instructions to the subject, to take an on-line course on proper pump usage. One or more on-line courses may be an option available from the subject-user's personalized website location (or other suitable website location) or may be automatically sent (pushed) to the subject-user's computer 14 during a communication session between the subject-user and the system 16.

Other information that may be communicated to a subject-user (or group of subject-users) includes treatment recommendations. Such treatment recommendations may be stored on the system 16 in one or more previous communication sessions between the system 16 and a healthcare provider-user or, in some embodiments, authorized personnel (such as physicians or other trained medical personnel) associated with the system 16. Such treatment recommendations may include instructions to the subject-user (for example, but not limited to, instructions relating to operating or settings a subject support device, meals or diet, exercise or other activities of the subject-user). Treatment recommendations may include recommended new or modified operating parameters or other settings that may be applied to a subject support device for controlling the operation of the subject support device. In this regard, a subject-user may opt to access treatment recommendations that have been issued by a healthcare provider-user or other authorized personnel, based on the healthcare provider's (or other authorized personnel's) analysis of information available on the system 16.

Alternatively, or in addition, the healthcare provider-user may cause the system 16 to automatically communicate electronic device control instructions to the subject support device 12, during an Internet communication session as described above. For example, the system 16 may communicate control instructions to a subject's subject-side computer 14, during an Internet communication session. The subject-side computer 14 may store such control instructions, at least temporarily. Then, either during the same Internet session or at some time after that Internet session, the subject support device 12 may be coupled for communication with the subject-side computer 14, as described above, to receive the control instructions from the subject-side computer 14. Such control instructions may include new operating parameters and/or instructions for causing the subject support device to change one or more of its operating parameters. For example, in contexts in which the subject support device is a medical infusion pump (such as an insulin infusion pump), operating parameters may include pumping rates and pumping time periods, such as pump basal rates and times, bolus rates and times, or the like.

Procedures for communicating new software, software updates or the like to a subject support device 12 may include suitable protective measures for improving accuracy and to inhibit an inadvertent loss of functions or data from the subject support device. For example, when replacing, adding or modifying software on the subject support device 12 and/or the subject-side computer 14, the device 12 and/or computer 14 may be controlled to provide or define two separate memory spaces, one for the current version of software and another for a new or modified software. In that manner, the original version may be saved or remain in memory as a back-up, in the event that the new or modified software is not properly received or is otherwise not functional. The system 16, device 12 and/or computer 14 may be controlled to switch from a new or modified software stored in a second memory space to an original software stored in the a memory space, in the event that the system 16, device 12 and/or computer 14 detects that the new or modified software is not properly received or does not function properly.

Yet further optional activities or resources may be available to the subject-user on the medical data management system 16 including, for example, an option for the subject-user to customize or otherwise further personalize the subject-user's personalized website location. In particular, from the subject user's personalized web page (box 60 in FIG. 3), the subject-user may select an option to customize the personalized web page. When the system 16 receives such a request from a subject-user (box 98 in FIG. 3), the system 16 may provide the subject user with a list or other arrangement of multiple selectable icons or other indicia representing parameters that may be modified to accommodate the subject-user's preferences (box 100 in FIG. 3). When a subject-user selects one or more of the icons or other indicia, the system 16 may receive the subject-user's request and makes the requested modifications to the subject-user's personalized web page location (box 101).

Following the receipt of modification parameters from a subject-user (box 101), the system 16 may again prompt the subject-user to select an activity or resource available on the system 16, for example, by being returned to the subject-user's personalized user website location (box 60). Alternatively, or in addition, if no further activities are to be performed with the system 16, the communication session may be ended, as represented by box 74.

Healthcare Provider-User Processes:

Each subject-user may designate one or more healthcare provider for connection to the system 10 through one or more respective healthcare provider computers 20, for example, to access the subject's information stored in the medical data management system 16. In this manner, a subject may designate the subject's primary physician for connection to the system 10 as a healthcare provider-user for the subject. Alternatively, or in addition, other physicians, medical technicians, or the like may be designated for connection to the system 10 by a subject, by a subject's previously designated healthcare provider or by another person authorized to designate healthcare provider's. Designations may be made, for example, during a subject-user's registration process or as a further option available to the subject-user from the subject-user's personal website location (or other location on the system 16 website). Alternatively, or in addition, designations may be made or confirmed by the designator, through the mail, in person or by other procedures for providing a suitable level of security The system 16 (alone or in conjunction with software 21 residing on healthcare provider computers 20) may provide functions for limiting access rights of healthcare providers, for example, to allow access to data of only those subjects for which the healthcare provider has been predestinated and no other subjects. Other appropriate access restrictions may be imposed on one or more of the healthcare provider-user's ability to access certain information on the system 16 (for example, some, but not all of a particular subject's information or of groups of subjects' information may be accessed), depending upon the role of the particular healthcare provider.

Thus, in example embodiments, upon successful verification of a healthcare provider-user's identification information and password (box 52 in FIG. 2), the healthcare provider may be allowed access to information, including certain secure information stored on the system 16, based on the access rights and restrictions allocated by the system 16. For example, the healthcare provider-user may perform many of the same functions shown in FIG. 3 that may be performed by a subject-user (or that may be performed by the particular subject-user(s) who designated that healthcare provider for connection to the system 10). Such functions may include, but are not limited to, accessing general information made available on the system 16 website to all subjects or groups of subjects, accessing a subject's personal website location, accessing specific information about a subject or group of subjects, or generating or customizing reports regarding a subject's (or group of subject's) medical condition(s) or that subject's (or group of subjects') medical device(s) 12. As described above, access rights of each healthcare provider-user may be limited to subject information for subjects or groups of subjects for which the healthcare provider has previously been designated. In other embodiments, other suitable access limitations may be imposed to provide the healthcare provider with access to some or all other subject-user's information stored on the system 16, but with limitations imposed to avoid compromising such subject user's identity and/or confidential information.

Additionally or alternatively, the healthcare provider-user may couple one or more subject support devices 12 to the healthcare provider computer 20, for example, to download data or other information from the subject support device(s) 12 to the system 16, upload data, programs, program updates or other information from the system 16 to the subject's support device(s) 12, or manually enter information into the system 16 or to modify the subject's custom settings. Thus, for example, the healthcare provider-user may have a suitable communication device (such as a cradle or other communication connection as described above), for coupling a subject support device 12 to the healthcare provider computer 20, in a manner similar to that described above for coupling a subject support device 12 to a subject-side computer 14. As a result, the healthcare provider-user may connect a subject's support device(s) 12 to the system 10 when the subject visits the healthcare provider's office, for example, to initialize or reset operating parameters on the subject's support device 12, to collect data, to generate reports or perform other functions described above with respect to the subject-user.

In addition or as an alternative to performing functions that a subject-user may perform, in further embodiments a healthcare provider-user may perform other functions on the system 10, through the healthcare provider's computer 20. For example, a healthcare provider may access information stored on the system 16 for the specific healthcare provider, a predefined group of healthcare providers or all healthcare providers. The healthcare provider may access information regarding subjects designating that healthcare provider or, in further embodiments, to groups or populations of subjects to allow the healthcare provider to make population-based trend analysis, for example, to evaluate the effect of a treatment, activity or condition among populations of subjects. In addition or alternatively, a healthcare provider may cause new or revised treatment plans to be provided to a subject or group of subjects, access and accept or deny treatment recommendations issued by system 16 personnel, and/or have payment requests sent or otherwise provided to payers.

In example embodiments described with reference to FIG. 4, upon successful verification of a healthcare provider-user's identification information and password (box 52 in FIG. 2) a healthcare provider-user may be provided a secure, personalized website location assigned to the healthcare provider or to a pre-defined group of healthcare providers, as represented by box 110 in FIG. 4. The system 16 may provide personalized website locations that are based on the user's role, such that healthcare provider users are provided with personalized websites that include selectable options, information or resources that are particularly suited for healthcare providers, while subject user's are provided with personalized websites that include selectable options, information or resources more particularly suited for the subject user. Thus, the role of the user may be employed by the system 16 to determine the type of website options, information and resources to provide the user.

The healthcare provider's personal website location may provide a personalized home screen, including selectable icons or menu items for selecting optional activities, including, for example, options described above with reference to FIG. 3. However, for simplifying the drawing, FIG. 4 does not include boxes representing the options shown in FIG. 3 and, instead, illustrates yet further example options that may be available to a healthcare provider-user as an alternative or in addition to the options shown in FIG. 3.

Figure 4:
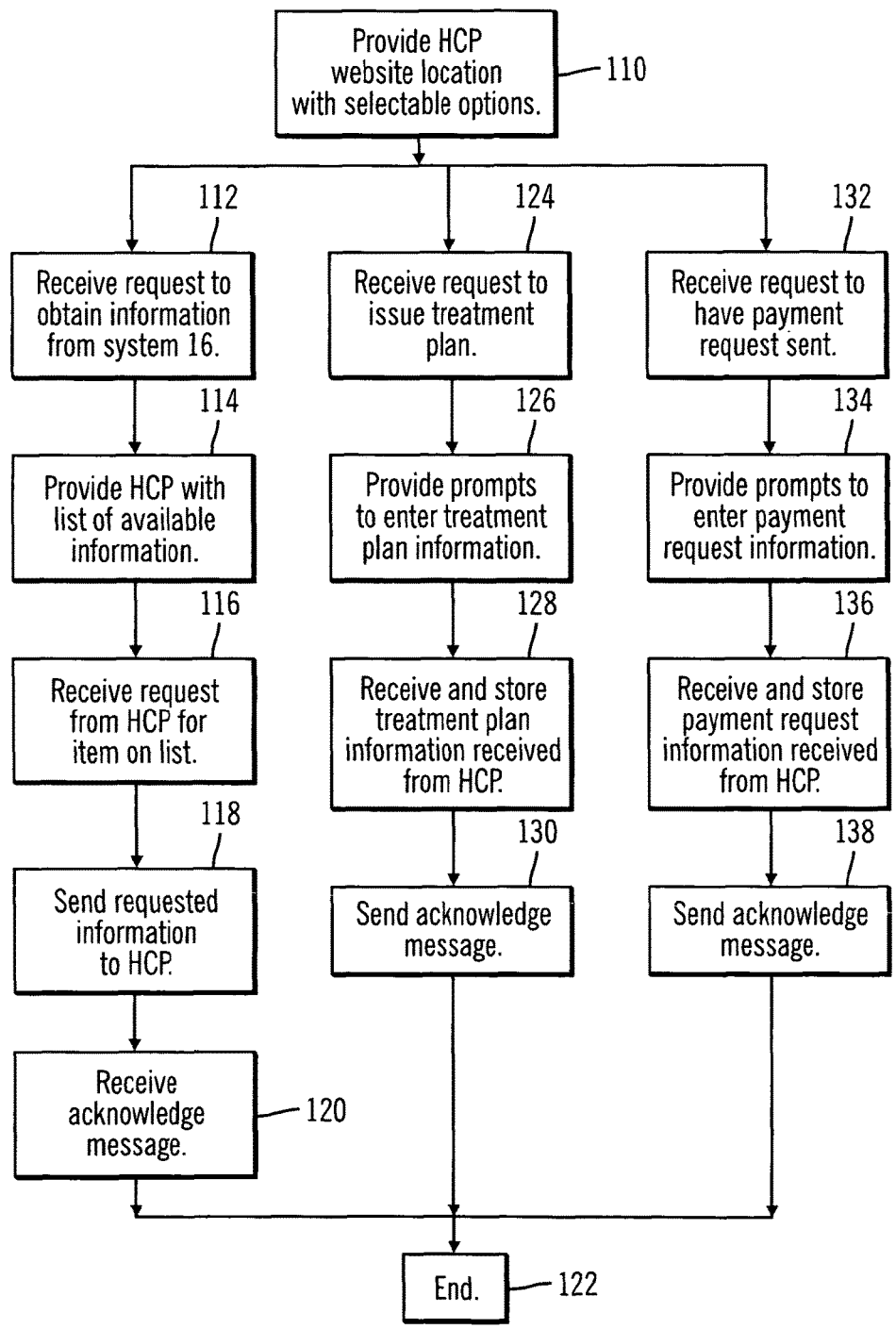
FIG. 4 is a generalized flow chart showing examples of optional processes for healthcare provider-users.

In FIG. 4, upon providing the healthcare provider-user with a plurality of user-selectable options for resources on the user's personalized website location (box 110), the healthcare provider-user may select an option to access information stored on the system 16 for the specific healthcare provider, a predefined group of healthcare providers or all healthcare providers. In addition, the healthcare provider-user may be provided with options for accessing information stored on the system 16 regarding subject-users for which the healthcare provider-user is designated and, in some embodiments, other subject-users, as described above. The healthcare provider-user may access, generate or customize reports, for example, as described above with respect to similar activities of the subject-user.

For example, from the healthcare provider-user's personal website location (box 110 in FIG. 4) or another suitable location on the system 16 website, the healthcare provider-user may select an option to receive data, reports, software, software updates, treatment recommendations or other information from the system 16 on the healthcare provider's computer 20. If the system 16 receives a request from a healthcare provider-user to receive data, reports, software, software updates, treatment recommendations or other information (box 112 in FIG. 4), the system 16 may provide the healthcare provider-user with a list or other arrangement of multiple selectable icons or other indicia representing available data, reports, software, software updates, treatment recommendations or other information available to the user (box 114 in FIG. 4). When a healthcare provider-user selects one or more of the icons or other indicia, the system 16 may receive the healthcare provider-user's request for data, reports, software, software updates, treatment recommendations or other information (box 116) and transmits the requested information to the healthcare provider's computer 20 and/or a subject support device 12 connected thereto (box 118).

Alternatively, or in addition, some or all of the data, reports, software, software updates, treatment recommendations or other information available to the healthcare provider-user may be automatically communicated to the healthcare provider's computer 20 upon the system 16 receiving a general request to obtain information (box 112) and without the need for the user to receive a list and individually select information items from the list (boxes 114 and 116). Alternatively or in addition, the system 16 and/or the system software 21 residing on the healthcare provider's computer 20 may be configured to provide the healthcare provider-user with data, reports, software, software updates, treatment recommendations or other information automatically during a communication session with the system 16 (without requiring the user to select an option to upload such information in box 112).

As represented by box 120, the system software 21 residing on the healthcare provider's computer 20 may cause the healthcare provider's computer to send an acknowledgment message back to the medical data management system 16, and the system 16 may receive such an acknowledgment message over the Internet, for example, upon a successful receipt by the computer 20 of information from the system 16. The healthcare provider-user may be prompted again to select an activity or resource available on the system 16, for example, by being returned to the healthcare provider-user's personalized user website location (box 110). Alternatively, or in addition, if no further activities are to be performed with the system 16, the communication session may be ended, as represented by box 122.

By providing the system 16 with the capability to forward data, software, software updates or other information to healthcare provider-users throughout the system 10, each healthcare provider-user may be provided with the most updated versions of software for controlling the subject's support device(s) 12, the most updated versions of the system software 21 residing on the healthcare provider's computer 20 and/or the most updated general or subject-specific information. In this manner, the medical data management system may be employed to help manage healthcare provider-users on the system 10, to provide a more comprehensive and consistent usage of the most appropriate and advanced products and services available to the healthcare provider-users.

In association with the option to prepare reports of subject information (by accessing existing types of reports, designing original reports or modifying reports), a healthcare provider-user may provide a report (or parameters for generating a report) to a subject-user or group of subject-user's. In particular, the healthcare provider-user may be provided with an option to store a particular report or report parameters for later access by a subject or group of subjects. The report and/or parameters may be stored on the system 16 database. As a result, a healthcare provider-user may select an existing type of report or design a report that the healthcare provider believes would be helpful to a particular subject or group of subject's (for example, based on the healthcare provider's assessment of the subject's or group's medical condition, habits, ability to understand reports, or other personal information that may be available to the particular healthcare provider treating that subject or group).

Another optional activity or resource that may be available to the healthcare provider-user may be an option to access treatment recommendations that may have been stored on the system 16 database, in one or more previous sessions of other healthcare provider-users or system 16 personnel. Thus, in example embodiments, certain pre-designated healthcare provider-users may have been authorized to store treatment recommendations for one or more particular subject-users (or group of subject-users). In further example embodiments, certain pre-designated personnel associated with the entity operating the system 16 (such as physicians or other trained medical personnel employed by or otherwise associated with the entity) may have been authorized to store treatment recommendations on the system 16 database for all subject-users or, in other embodiments, for certain pre-designated subject-users (or groups of subject-users). Thus, a healthcare provider-user who is designated for treating a particular subject-user (or group of subject-users) may access treatment recommendations stored on the system for that subject-user (or group of subject-users).

Depending upon the nature of the treatment recommendation, the healthcare-provider user accessing the treatment recommendation may have further options. In one example embodiment, the treatment recommendation may include observations or instructions directed to assist the healthcare provider's own analysis of subject information available on the system 16. In further example embodiments, the treatment recommendation may include instructions, operating parameters or other information that may be passed on to the subject-user, to assist the subject-user or otherwise improve the subject-user's medical treatment. In such an embodiment, the healthcare provider-user may be provided with an option (such as one or more selectable icons) that allows the healthcare provider to accept the treatment recommendations and provide them to the subject-user (or group of subject-users). Upon acceptance of a treatment recommendation, the system 16 may make the treatment recommendation accessible to the subject-user (or group), for example, by automatically sending the treatment recommendation to the subject-user in the next (or subsequent) communication session between the subject-user and the system 16 or in any other manner as described above for allowing subject-user access to system information.

Yet another optional activity or resource that may be available to the healthcare provider-user may be an option to have new or revised treatment plans or treatment recommendations provided to a subject or group of subjects. For example, a healthcare provider may receive information, including data, reports or treatment recommendations regarding a subject-user or a group of subject-users, evaluate the information and issue a new or revised treatment for the subject (or for a group of subjects) based on the evaluation.

The healthcare provider-user may receive subject information in any suitable manner, such as from the medical data management system 16, a subject's support device(s) 12, a subject-side computer 14 connected to the system 10, and/or directly from the subject (such as by examining the subject). For example, a healthcare provider-user may receive subject information and reports from the system 16 in the manner described above with respect to boxes 112-120 in FIG. 4. Alternatively or in addition, a healthcare provider-user may receive information from a subject's support device(s) 12 by coupling the support device(s) to the healthcare provider's computer 20 in the manner described above (for example, during a subject's visit to the healthcare provider's office or as part of an initialization procedure performed by the healthcare provider before issuing a new subject support device 12 to a subject). Alternatively or in addition, the system 16 and system software 21 and 19 residing on the healthcare provider's computer 20 and the subject-side computer 14, respectively, may cooperate to allow a subject-user to couple one or more subject support devices 12 to a subject-side computer 14 connected to the system 16 through the Internet, while a healthcare provider simultaneously accesses information from the subject support device(s) 12 and/or the subject-side computer 14, through an Internet connection to the system 16.

Based on the healthcare provider's evaluation of subject information received on the system 10, the healthcare provider may determine that a new or revised treatment scheme would be appropriate for a subject or group of subjects for which the healthcare provider is designated. In some embodiments as described above, a healthcare provider may also access treatment recommendations that may have been stored on the system database for the subject or group of subjects, to assist the healthcare provider with evaluating the subject information and making intelligent treatment plans for the subject or group of subjects. Once the healthcare provider-user determines a new or modified treatment plan, the healthcare provider-user may select an option from the healthcare provider-user's personal website location or other suitable website location, to modify a subject-user's (or group of subject-user's) treatment plan, as represented by box 124 in FIG. 4.

In response, as shown in box 126, the system 16 (or software 21 residing on the healthcare provider's computer 20) may instruct or otherwise prompt the healthcare provider-user to input treatment information regarding the patent and the new or revised treatment scheme, such as instructions to a subject, the subject's support device(s) 12 and/or the subject's computer 14. The healthcare provider may enter such treatment information through a suitable user interface (keyboard, mouse, touch screen, optical interface or the like) on the healthcare provider's computer 20 and send the information to system 16, for example, over the Internet connection.

The system 16 may receive and store the treatment information for later retrieval by a subject-user, as represented by box 128 in FIG. 4. Alternatively, or in addition, in the event that the subject support device(s) is coupled for communication in the system 10 at the same time that the healthcare provider is sending treatment information, the system 16 may pass the treatment information to the subject support device(s) 12 (or to the subject computer 14 through which the device(s) 12 are coupled). In yet further embodiments, one or more treatment plans may be communicated to the system 16 in other suitable forms, such as through the postal mail or by hand delivery (where a system administrator receives postal mail or delivery and enters the treatment plan into the system through an system administrator's computer 18). Suitable security measures may be implemented to restrict the ability of a healthcare provider-user to issue treatment plans to subject-users, for example, such that a healthcare provider may only issue treatment plans for subject-users who have designated or otherwise authorized that healthcare provider to issue treatment plans for them.

Treatment plans may be developed by healthcare provider-users for specific subjects or groups of subjects, based on an evaluation of individual subject trends or group trends. For example, a healthcare provider may access and evaluate information regarding a defined study group of subject-users. In one example, a healthcare provider may define a study group (for example, subjects with a specified medical condition, subjects under or over a specified age, subjects of a specified gender, or other medically-relevant characteristic), based on a treatment theory or fact. In further embodiments, the system 16 may provide healthcare provider-users with selectable options for various types of study groups of subject-users, where such groups have been pre-defined by, for example, a system operator or administrator. Such pre-defined groups may be groups of pre-designated, specific subjects or groups of subjects that have pre-designated, specific characteristics (such as, but not limited to, age, gender, medical condition, length of time of the medical condition, length of treatment time, type of treatment, geographic or other demographic information, or the like). By evaluating trends occurring in groups of subject-users, a healthcare provider-user may be able to identify and design a treatment that could be considered a "best practices treatment" for one or more subjects, such as one or more subjects within the group or for other groups of subjects.

In such embodiments, the healthcare provider-user may access information or reports for the defined group from the system 16. By evaluating the study group information, the healthcare provider-user may be able to develop a treatment plan or algorithm for a subject or group of subjects. The treatment plan or algorithm may be designed, for example, to cause the subject or group of subjects under treatment to develop characteristics more or less like the subjects in the study group.

Treatment information issued by a healthcare provider may be directed to a particular subject or group of subjects (such as a particular subject or group for which the issuing healthcare provider is designated). In such a case, the treatment information may be stored in one or more subject-specific storage locations in the system database 29. Such treatment information may be made available by the system 16 to the particular subject or group of subjects to which it is directed (and/or to that subject's support device(s) 12 or computer 14), for example, as a selectable option from the subject-user's personal website location or other suitable location on the system 16 website. Alternatively, or in addition, such treatment information may be automatically communicated to the subject-user (and/or to that subject's support device(s) 12 or computer 14), upon the subject-user accessing the system 16 website (without the need for the subject-user to select an option to receive treatment information).

In embodiments in which treatment information is automatically communicated to the subject's support device(s) 12 (either directly or through an initial storage in the subject-side computer 14), the treatment information may comprise parameters for automatically setting or adjusting the operation of the subject support device (12). In this manner, a subject's support device(s) 12 may be automatically set or configured in accordance with the subject's healthcare provider's treatment plan, by connecting the subject support device(s) 12 into the system 10 for communication with the medical data management system 16.

In embodiments in which the treatment information includes individual identifiers associated with the subject, the system 16 (and/or software 19 and 21 residing on the subject-side computer 14 and the healthcare provider's computer 20, respectively) may provide suitable security measures during the communication of such information, such as, but not limited to encryption, authentication procedures, validity checks, or the like. Alternatively, or in addition, the storage in the system database 29 of any treatment information that includes individual identifiers associated with a subject may be carried out with suitable security measures, such as, but not limited to, the use of one or more separate, secure storage devices or storage areas for any information that includes individual identifiers, as described above.

In certain example embodiments, a healthcare provider may issue a treatment plan that involves adjustments or modifications to a treatment or other activities in response to events or activities in the subject's information received from, for example, a subject support device. Thus, a healthcare provider-user may issue a script of one or more treatment activities, adjustments or modifications that become effective if the subject support device information received by the system from a subject-user reaches or crosses a pre-defined threshold or otherwise indicates that a medically relevant event has or is likely to occur. In further embodiments, the healthcare provider-user may make the treatment activity, adjustment or modification become effective upon the occurrence of other events, such as the entry of particular manual information into the system by a subject-user, the lapse of a pre-defined period of time, the occurrence of a pre-defined time of day or date, or combinations thereof. In yet further embodiments, a healthcare provider-user may make a treatment activity, adjustment or modification become effective upon occurrence of a combination of one or more of a threshold event and/or one or more of a time or date event or a manual entry event.

For example, the medical data management system 16 may receive and store a treatment plan from a healthcare provider (boxes 128 in FIG. 4) designated for a given subject-user, wherein the treatment plan involves adjustments to the subject-user's treatment in the event that certain conditions are present in subject information (such as subject support device data) received by the system 16. The treatment plan may include one or more specific adjustments (such as, but not limited to, a specified increase or decrease in the dosage of a specified medication, in the event that a specified, sensed biological value crosses a defined threshold) and/or a more elaborate algorithm that defines treatment changes deepening upon one or more characteristics in one or more sensed biological values.

The system 16 also may receive subject information, such as subject support device data (boxes 62-72 in FIG. 3) and/or manually entered or logbook information (boxes 76-80 in FIG. 3). The system 16 may include a suitable routine (or set of routines) for evaluating received subject information for a given subject with stored treatment plan(s) for that subject and to determine if the treatment plan (or algorithm) specifies a change in treatment as a result of the subject information. An example of a flow chart of a treatment plan routine is shown in FIG. 5.

Figure 5:
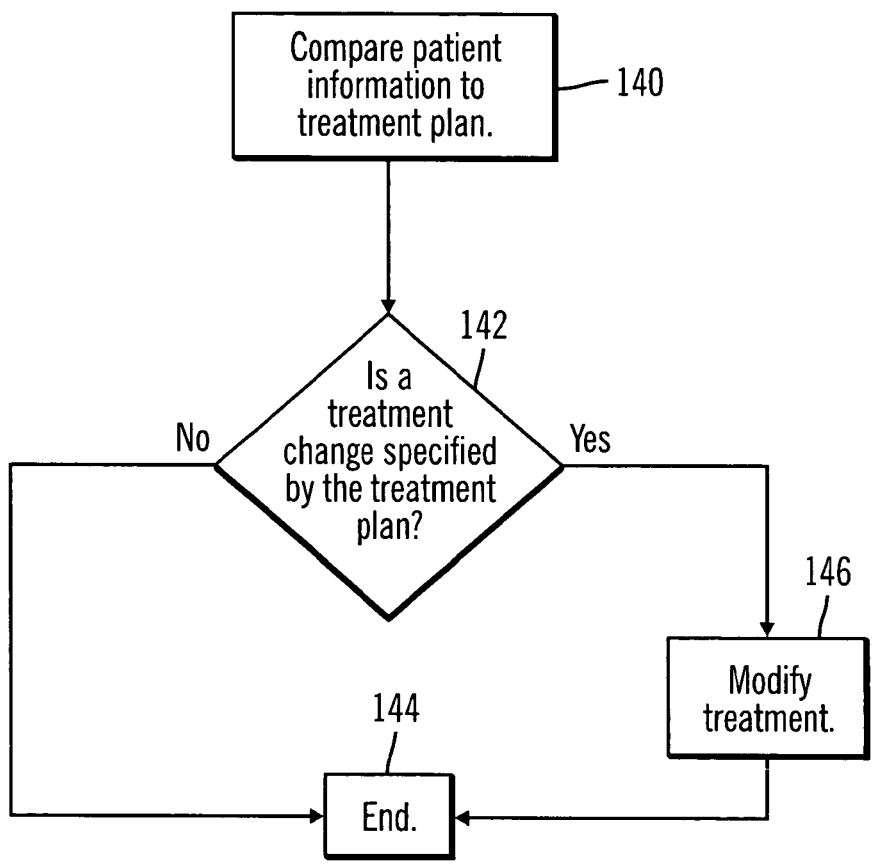
FIG. 5 is a generalized flow chart showing a process for providing a modifiable treatment plan.

With reference to FIG. 5, the routine(s) may cause the system 16 to take one or more actions, in the event that a change of treatment is determined. As represented by box 140, the system 16 compares (or otherwise evaluates) received subject information with stored treatment plan (or algorithm) instructions. Based on that comparison (or evaluation), the system 16 determines whether a change in the treatment is specified by the treatment plan, as represented by box 142. If not, the system 16 may end the routine (as represented by box 144). On the other hand, if the system 16 determines that a treatment change for a subject-user is specified by the treatment plan (or algorithm), then the system 16 may take further action to modify the subject-user's treatment, as represented by box 146.

Such further action may include providing a message to the subject-user and/or the healthcare provider who issued the treatment plan for the subject-user. Alternatively or in addition, the action taken by the system 16 to modify a treatment may include providing modification parameters for controlling a subject support device to the subject-user and/or the healthcare provider who issued the treatment plan. The message and/or treatment parameters may be sent by email, posted on the user's personal website location, posted or stored in other locations on the system database 29 for access by the relevant user, reported to the user through a telephone call from a system administrator, sent by postal mail and/or communicated by other suitable procedures. The message may include instructions for changing a treatment and/or request the user to contact a defined person or entity for further instructions. The modification parameters may include control data that may be loaded into the subject support device (for example, through a connection to the subject-side computer 14 or the healthcare provider computer 20, as described above), for controlling the operation of the at least one aspect of the subject support device.

Upon performing the treatment modification task (box 146 in FIG. 5), the system 16 may end the treatment modification routine (box 144). In further embodiments, some or all of the treatment modification routine may be carried out on the healthcare provider's computer 20, wherein treatment modification messages or parameters may be communicated from the healthcare provider's computer 20 to a subject support device 12 connected thereto, to a subject-side computer 14 through an Internet connection and/or to the system database 29 or other suitable storage location for later retrieval by the subject-user.

Also, while treatment modification embodiments may be applied to individual subject-users (wherein a separate modifiable treatment plan is provided for each individual subject-user), other embodiments may employ modifiable treatment plans that are applied to one or more groups of subjects. In such embodiments, individual subject-user information (from the subject support device(s) and/or manual entries of individual users) for each subject-user in a defined group is compared to a group treatment plan (or algorithm). The group treatment plan may be a modifiable plan (that modifies treatment upon the occurrence of pre-defined changes in subject information) applied commonly to each subject-user in the group. Thus, while a single, common treatment plan may be applied to all subject-users in a defined group, a given subject-user in the group may receive a different treatment from another subject-user in the group, due to differences in the subject information received from the two subject-users. In further embodiments, multiple common treatment plans may be applied to a defined group of subject-user's, such that each subject-user may receive a treatment based on any one or combination of the multiple treatment plans and the individual user's subject information.

A new or modified treatment plan may comprise, for example, but not limited to, new or revised dosages of an infusion media, infusion pump control parameters, revised maximum basal rate or bolus amount, temporary basal rate, bolus type, or the like. Pump control parameters may include parameters for controlling or changing a basal rate, bolus amount, infusion times, maximum basal or bolus, temporary rates, or the like.

In the context of a diabetes subject, an initial treatment may comprise, for example, an initial infusion rate of an insulin infusion medium (such as a basal rate), while a revised or modified treatment may comprise, for example, an increase or reduction in the initial infusion rate (such as, but not limited to, a temporary bolus or a more lasting adjustment of a basal rate). For a diabetes subject, the medical data that may trigger a change in the subject's treatment may comprise, for example, sensor data from a blood glucose sensor connected to the subject or a monitor operated by the subject. Thus, an healthcare provider for a diabetes subject (or group of diabetes subjects) may issue a treatment plan that involves an initial insulin infusion rate or program of rates and also involves a revised insulin infusion rate or program of rates that is implemented if the subject's sensed or monitored blood-glucose level exceeds or drops below one or more pre-defined threshold levels. In one example embodiment, high and low threshold levels may be set by the healthcare provider, to result in different treatment revisions in the event that the subject's medical data crosses the high and low threshold levels, respectively. Also, in further embodiments, a healthcare provider may issue a treatment plan that includes multiple thresholds for the same or different parameters in the subject's medical data, such that the subject's treatment may be revised in the event that any one of the thresholds are crossed. Furthermore, treatment plans may be issued in which multiple revisions to a subject's treatment are made, in the event that multiple thresholds are crossed.

A treatment plan for a subject may include an action taken upon a detection of an empty or low expendable resource, such as a low or empty supply of an infusion medium, battery power or other expandable resource. Thus, for example, a subject support device 12 may include suitable sensors for detecting the state of an expendable resource. Information relating to the state of the expendable resource may be communicated to the system 16 for storage and/or inclusion in reports or analysis as described herein. In certain embodiments, upon the detection of a low or exhausted state of a resource, the system 16 may issue a message to the subject-user (and/or to the subject's designated healthcare provider-user(s)), for example, to inform or warn the user of the exhausted or near exhausted state of the resource.

In further embodiments, in response to a detection of a low or exhausted state of a resource, the system may cause an updated resource to be sent to the subject-user (or to the designated healthcare provider-user) from a supply source, such as a new supply of infusion needle sets, a new supply of an infusion medium (insulin or other medium), a new battery, or other suitable resource. For example, the system 16 (and/or system software 19 or 21 residing on a subject-side computer 14 or on a healthcare provider-user's computer 20) may cause a purchase order (or other form of an order) to be sent to a supply source. For example, the order is placed by posting the order on a location on a system website available to supply source entities, sending the order by an email to one or more supply source entities, sending the order by postal mail or hand delivery to one or more supply source entities, or the like. Depending upon the embodiment and environment of use, the supply source entity may comprise a pharmaceutical store or distributor, medical products store or distributor, or the like. In response to receiving an order from the system 16, the supply source(s) may send updated resources, as needed, directly to the subject-user (or to the designated healthcare provider-user to give to the subject-user).

In one example embodiment, the expendable resource is an infusion needle set that connects an infusion pump to a subject. The needle set in such pumps must be replaced at certain intervals. When the needle set is replaced, the pump must be re-primed (to fill the tubing between the pump and the needle. Infusion pumps typically include a priming operation or mode for priming the system after a needle set is replaced. Also, certain infusion pumps include electronic storage devices that store historical pump operation information, including information regarding the occurrence of a pump priming event. By obtaining and evaluating historical pump operation information from a subject-user's infusion pump, the system 16 (and/or software 19 or 21) may determine a number of pump priming events that correspond to a number of infusion needle set replacements that have occurred. This information may be compared with a pre-stored value representing the number of infusion needle sets previously supplied to that subject-user to determine whether or not the subject-user requires additional infusion needle sets. If the comparison shows that additional needle sets are needed, then the system may cause an order to be placed for additional needle sets to be sent to the subject-user, as described above. Similar procedures may apply to other expendable resources.

In embodiments in which a healthcare provider is able to issue treatment plans (or modifiable treatment plans) through the system 16 and/or cause the system to update a subject's supply of a resource, additional measures may be implemented for the maintenance of proper authorization records, as may be required or recommended by government regulations, industry standards, policies or the like. For example, healthcare providers may be required to submit signed (or otherwise validated) original versions or copies of prescriptions or other records, that specify the healthcare provider's treatment plan. Such prescriptions or other records may be stored in an appropriate storage facility associated with the system 16. In one embodiment, electronic copies of such prescriptions or other records may be stored in the system database 29, for access by an authorized user. For example, electronic copies of such prescriptions or other records may be communicated to the system 16, from the healthcare provider's computer 20, over the Internet. Suitable security measures may be imposed by system 16 (and or software 21 residing on the healthcare provider's computer 20) for communication and/or storage of such prescriptions or other records, including, but not limited to encryption, password protection procedures, or the like.

Returning to the process of FIG. 4, the system 16 may send an acknowledgment message back to the healthcare provider's computer 20, upon receipt of treatment plan information from the healthcare provider-user, as represented by box 130 in FIG. 4. The healthcare provider-user may be prompted again to select an activity or resource available on the system 16, for example, by being returned to the healthcare provider-user's personalized user website location (box 110). Alternatively, or in addition, if no further activities are to be performed with the system 16, the communication session may be ended, as represented by box 122.

In addition to modifying an existing treatment plan, a healthcare provider-user may evaluate subject information (for an individual subject-user or for a group of subject-users) to develop an initial or starting treatment for a new subject or new group of subjects (or for an existing subject or group with a new subject support device). Thus, a healthcare provider-user may employ the system 16 to obtain subject information or reports and, based on an evaluation (or algorithm) involving the reported information, the healthcare provider-user may design initial operational parameters for starting a new treatment. For example, a healthcare provider-user may evaluate trends of that subject-user (from a sensor or meter included in the subject-user's subject support device 12) or of other diabetes subject-user's and design appropriate an appropriate initial treatment plan, including initial setting for a new subject support device 12. In the context of a diabetes subject-user, initial treatment or settings may include initial blood-glucose level test schedules, insulin infusion rates (such as an initial basal rate, initial bolus amounts and times, initial maximum bolus or basal, or the like for setting an insulin infusion pump), suggested subject diet or activities (such as amounts or times for exercise, sleep, ingestion of food or medicine) or the like.

Thus, the ability to access conglomerate subject information on the system 16 can allow a healthcare provider to determine a suitable starting point for a subject beginning a new treatment (such as using a new subject support device). In contexts in which the new treatment involves a subject support device that must be programmed or otherwise configured or set to operate in a certain manner, the healthcare provider-user may design appropriate setting parameters and provide the parameters to the subject-user. The subject-user may enter the parameters into or otherwise set the subject support device. Alternatively, or in addition, the healthcare provider-user may enter the parameters into and set the subject support device, before sending or otherwise supplying the subject support device to the subject. Thus, for example, a healthcare provider may obtain an insulin infusion pump for a diabetes subject from a suitable vendor from a suitable source and may evaluate conglomerate subject data, design pump settings and set the pump, before providing the pump to the subject.

In a further example embodiment, initial parameters (such as initial insulin pump setting parameters) may be determined for a subject as part of an initial start-up kit. The initial start-up kit may be provided to a subject-user (or the subject-user's healthcare provider), for starting a new treatment (for example, involving a new subject support device). Depending upon the embodiment and context of use, the start-up kit may include various materials, such as, but not limited to, test taking materials, instructive literature, nutritional aids, or the like. In some embodiments, the start-up kit may include the new subject support device 12 (prior to being initially set), while in other embodiments, the start-up kit does not include the subject support device.

For example, a start-up kit for a diabetes subject starting a treatment on a new insulin infusion pump may include blood glucose testing equipment (such as finger prick strips), one or more controlled meals and instructive literature regarding proper testing and pump operating procedure. With the start-up kit, a subject may conduct one or more controlled meal tests, according to the instructive literature, to determine initial parameters for initially setting the infusion rates and/or other parameters for a new insulin infusion pump for that subject.

A controlled meal test may involve the subject eating one or more of the controlled meals provided with the start-up kit. A controlled meal may be any one or combination of nutritional substances in known portions, that have known levels of carbohydrates. Such controlled meals may be prepared and packaged in known portions (with known carbohydrate levels) specifically for the kit. Alternatively, such controlled meal may be one or more commonly available food products that are packaged with labels that define the carbohydrate contents of the food product. For example, such packaged food products may include, but are not limited to, one or more nutritional bars, nutritional drinks (such as Ensure™ or the like), frozen food meals, or the like.

In one embodiment, instead of (or in addition to) providing one or more controlled meals with the kit, the instructive materials in the kit may instruct the user to obtain and use certain, identified food products that may be commonly available at stores local to the user.

Along with eating one or more controlled meals, a subject may take multiple, discrete blood-glucose tests throughout a defined period of time. The period of time may depend upon various factors, including the manner in which blood-glucose tests are taken, the subject's medical condition, the subject's daily activities and the like. In one embodiment, the blood-glucose tests may be taken with finger-prick strips that may be included in the start-up kit. In other embodiments, the subject-user may employ an electronic blood-glucose monitor or sensor (such as, but not limited to those described herein) to obtain blood-glucose test results.

Based on the known level(s) of carbohydrate intake (from the controlled meal(s)) and also based on the blood-glucose tests, the system 16 (and/or system software residing on the user's computer) may determine the subject-user's rate of change of blood-glucose level per amount of carbohydrate intake, $\Delta BG$/gram of carbohydrate. Thus, with the knowledge of the user's carbohydrate sensitivity, a user's blood-glucose level (BG) may be estimated for future nutritional intakes (meals, snacks, etc.) by estimating or otherwise obtaining the carbohydrate content of the nutritional intake. The insulin pump may include an input for allowing a user (the subject or a healthcare provider) to enter information, such as a value, representing the subject's carbohydrate sensitivity, $\Delta BG$/gram of carbohydrate (such as determined in one or more controlled meal tests described above), as an initial parameter.

Figure 6A:
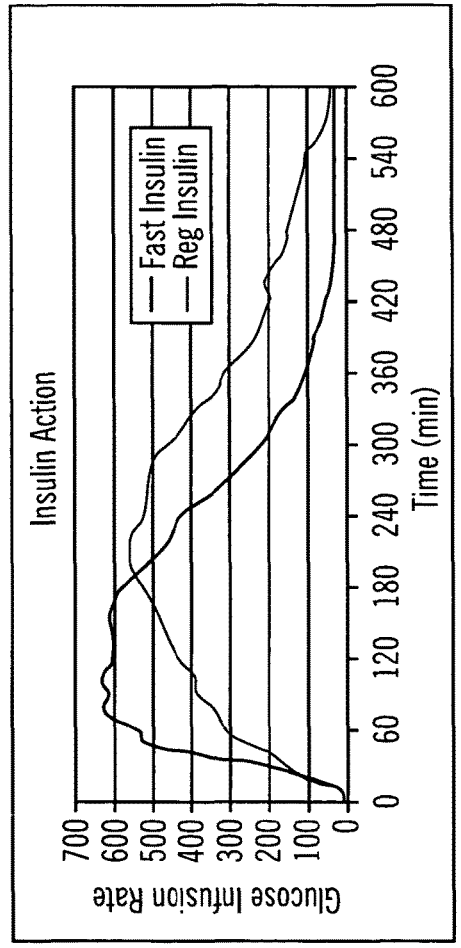
FIGS. 6a and 6b are examples of insulin activity curves representing the blood-glucose level of a diabetes subject upon an event.
Figure 6B:
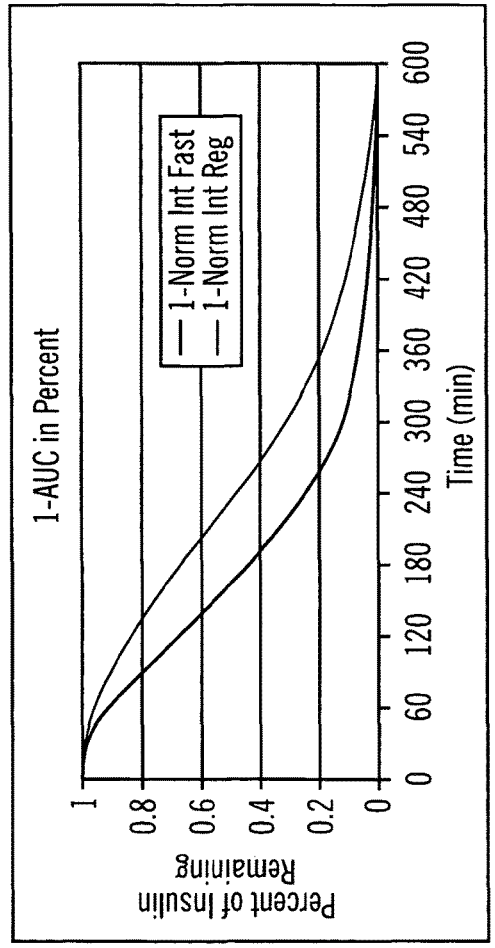

An insulin activity curve of BG over time ($\Delta BG$), such as shown in FIG. 6a, may be provided for the subject-user. The insulin activity curve of FIG. 6a is based on the curve shown in FIG. 6b. In FIG. 6b, an insulin action curve is a plot of glucose infusion rate during an insulin clamp. This curve shows how long a subcutaneous injection of insulin works and the pharmacodynamics of insulin action. The curve in FIG. 6b is an insulin action curve, plotting the insulin action remaining after a bolus injection of insulin into a subject's abdomen. This data is obtained by first integrating the curve in FIG. 6a and then subtracting the area under the curve (AUC) from the integral. The curve in FIG. 6b may be used in a bolus estimator program for calculating insulin amounts. The curve in FIG. 6a and/or 6b may be stored in the insulin pump electronics (for example, as data, one or more mathematical formulas or other information representing the curve). In further embodiments, multiple optional curves may be stored in the insulin pump, such that an appropriate curve is selected for the particular user as a starting curve.

The insulin activity curve may have a high level (x) representing the estimated BG after an event, such as a nutritional intake of a known or estimated carbohydrate level. The level (x) may be a value determined from a algorithm carried out by the insulin pump electronics, for example, by multiplying the known or estimated grams of carbohydrate entered by the subject into an input on the insulin pump upon eating a meal or snack with the previously entered carbohydrate sensitivity ($\Delta BG$/gram of carbohydrate) of the subject.

The insulin activity curve of a typical diabetes subject slopes downward, in a backward "S" shape, toward a target level (which may be set by a healthcare provider), following an event such as a nutritional intake. The target level is the desired BG level for the subject. In one embodiment, the insulin activity curve is initially defined as an estimated curve for the subject, for example, based on common, historical data from other subjects. In other embodiments, the insulin activity curve for the subject may be derived by providing insulin to the subject and taking BG tests of the subject, over a period or periods of time. Based on the shape of the insulin activity curve, the estimated or otherwise determined value (x) for BG after an nutritional event and the target value, an algorithm determines how much insulin is needed to direct the blood glucose level to the target level. The algorithm may employ an estimated or otherwise derived insulin sensitivity of the subject, ΔBG/unit of insulin to determine appropriate insulin amounts to direct the subject's BG toward the target level, along the insulin activity curve. The insulin sensitivity of the subject may be another parameter entered into the pump electronics through a user-input on the insulin pump.

In the above-described start-up environment, an initial insulin activity curve (such as shown in FIG. 6b) may be estimated or otherwise determined for a subject-user for purposes of starting a new or modified treatment plan. In further embodiments, the insulin activity curve for a subject (or group of subjects) is refined, based on data collected by the system 16 from the subject (or group of subjects) over a period of usage of the new or modified treatment plan. In yet further embodiments, published or documented guidelines or best clinical practice guidelines may be employed instead of (or in combination with) controlled meal tests.

Another optional activity or resource that may be available to the healthcare provider-user may be an option to have payment requests sent to payers. For example, from the healthcare provider-user's personal website location (box 110 in FIG. 4) or another suitable location on the system 16 website, the healthcare provider-user may select an option to have a payment request sent to a payor, and the system 16 may receive the user's selected option over the Internet, as represented by box 132 in FIG. 4.

In response, as shown in box 134, the system 16 (or software 21 residing on the healthcare provider's computer 20) may instruct or otherwise prompt the healthcare provider-user to input payment request information, such as, but not limited to, payor entity identification information, amount of payment due, subject identification information and/or a description of services rendered for which payment is being requested. The healthcare provider-user may enter such payment request information through a suitable user interface (keyboard, mouse, touch screen, optical interface or the like) on the healthcare provider's computer 20 and send the information to system 16, for example, over the Internet connection.

The system 16 may receive and store the payment request information for later retrieval by a payor entity-user, as represented by box 136 in FIG. 4. In one example embodiment, the system 16 (and/or software 21 residing on the healthcare provider's computer 20) may generate and send an email to the payor entity, upon the healthcare provider issuing payment request information, wherein the email may contain a notice to the payor entity that payment request information has been issued (and is stored on the system 16) and/or may contain a request for payment such as, but not limited to, an invoice. The email to the payor entity computer 22 may be generated and sent automatically upon the healthcare provider-user's submission of payment request information to the system 16. Alternatively, the email to the payor entity computer 22 may be generated and sent in response to a receipt by the system 16 (or the software 21) of a confirmation from the healthcare provider to send the email. Alternatively, or in addition, in the event that the payor entity-user is coupled for communication in the system 10 at the same time that the healthcare provider-user is sending payment request information to that payor entity-user, the system 16 may pass the payment request information to the payor entity's computer 22.

In embodiments in which the payment request information includes individual identifiers associated with the subject, the system 16 (and/or software 21 and 23 residing on the healthcare provider's computer 20 and the payor entity's computer 22, respectively) may provide suitable security measures during the communication of such information, such as, but not limited to encryption, password protection, authentication procedures, data validity procedures, or the like. Alternatively, or in addition, the storage in system database 29 of any payment request information that includes individual identifiers associated with a subject may be carried out with suitable security measures, such as, but not limited to, the use of one or more separate, secure storage devices or storage areas for any information that includes individual identifiers, as described above.

The system 16 may send an acknowledgment message back to the healthcare provider's computer 20, upon receipt of payment request information from the healthcare provider-user, as represented by box 138 in FIG. 4. The healthcare provider-user may be prompted again to select an activity or resource available on the system 16, for example, by being returned to the healthcare provider-user's personalized user website location (box 110). Alternatively, or in addition, if no further activities are to be performed with the system 16, the communication session may be ended, as represented by box 122.

Payor Entity-User Processes:

Each subject-user may designate one or more payor entities for connection to the system 10 through one or more respective payor entity computers 22, for example, to access some or all of the subject's information stored in the medical data management system 16. In this manner, a subject may designate the subject's medical insurance carrier or other medical coverage personnel or entity, for connection to the system 10 as a payor entity-user for the subject. Alternatively, or in addition, a payor entity may be designated for connection to the system 10 by a subject's designated healthcare provider or by another person authorized to designate payor entities. Designations may be made, for example, during a subject-user's registration process or as a further option available to the subject-user from the subject-user's personal website location (or other location on the system 16 website). Alternatively, or in addition, designations may be made or confirmed by the designator, through the mail, in person or by other procedures for providing a suitable level of security.

The system 16 (alone or in conjunction with software 23 residing on payor entity computers 22) may provide functions for limiting access rights of payor entities, for example, to only allow access to data of subjects for which the payor entity has been predesignated. Other appropriate access restrictions may be imposed on one or more of the payor entity-user's ability to access certain information on the system 16 (for example, some, but not all of a particular subject's information may be accessible), depending upon the role of the particular payor entity.

Thus, in example embodiments, upon successful verification of a payor entity-user's identification information and password (box 52 in FIG. 2), the payor entity may be allowed to access information, including certain secure information stored on the system 16, based on the access rights and restrictions allocated by the system 16. In this manner, an authorized payor entity may be able to access and review payment request information submitted to the payor entity by one or more healthcare providers. In more comprehensive embodiments, the payor entity-user may also be allowed access to certain medical data, reports and other information available on the system 16, to help the payor entity evaluate payment requests received from healthcare providers.

For example, the payor entity-user may perform some of the same functions shown in FIG. 3 that may be performed by a subject-user (or that may be performed by the particular subject-user(s) who designated that payor entity for connection to the system 10). Such functions may include, but are not limited to, accessing general information made available on the system 16 website to all subjects or groups of subjects, accessing a subject's personal website location, accessing specific information about a subject or group of subjects, or generating or customizing reports regarding a subject's (or group of subject's) medical condition(s) or that subject's (or group of subjects') medical device(s) 12. As described above, access rights of each payor entity-user may be limited to subject information for subjects or groups of subjects for which the payor entity has previously been designated. In other embodiments, other suitable access limitations may be imposed to provide the payor entity-user with access to some or all other subject-user's information stored on the system 16, but with limitations imposed to avoid compromising such subject user's identity and/or confidential information.

In addition or as an alternative to performing some of the functions that a subject-user may perform, in further embodiments a payor entity-user may perform other functions on the system 10, through the payor entity's computer 20. For example, a payor entity-user may access information stored on the system 16 for the specific payor entity, all payor entities, or a predefined group of payor entities of which that payor entity belongs. In addition or alternatively, a payor entity-user may access payment request information stored on the system 16 for that payor entity, and/or payment status information.

In example embodiments described with reference to FIG. 7, upon successful verification of a payor entity-user's identification information and password (box 52 in FIG. 2) a payor entity-user may be provided a secure, personalized website location assigned to the payor entity or to a predefined group of payor entities, as represented by box 150 in FIG. 6. As described above with respect to the healthcare provider personal websites, payor entity personal websites may be configured to include selectable options, information and resources that are particularly suited for payor entities. The system 16 may provide personalized website formats and content, based on the user's role as a subject, healthcare provider or payor entity.

The payor entity's personal website location may provide a personalized home screen, including selectable icons or menu items for selecting optional activities, including, for example, some of the options described above with reference to FIG. 3 (such as viewing or generating reports). However, for simplifying the drawing, FIG. 7 does not include boxes representing the options shown in FIG. 3 and, instead, illustrates yet further example options that may be available to a payor entity-user as an alternative or in addition to the options shown in FIG. 3.

Figure 7:
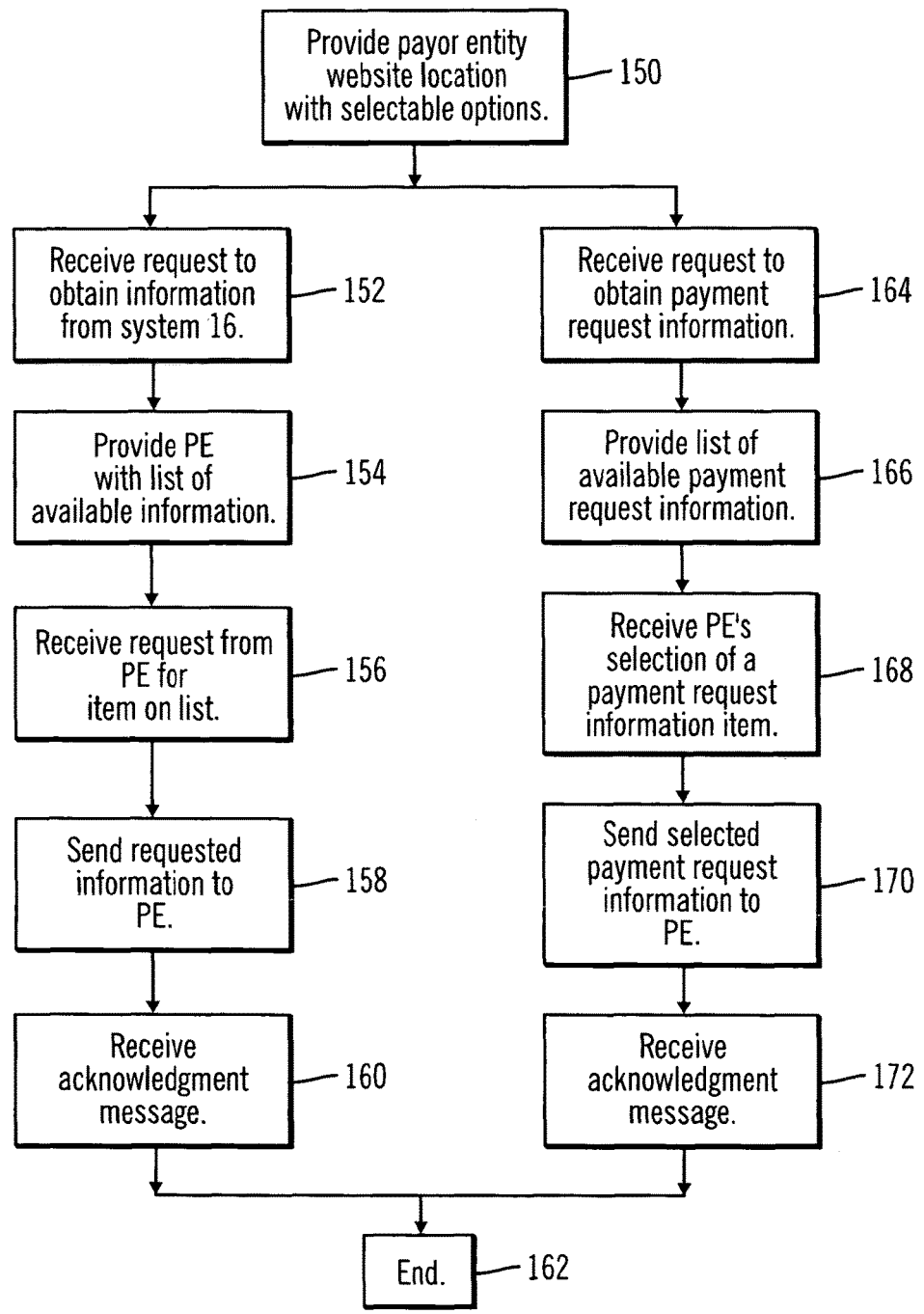
FIG. 7 is a generalized flow chart showing examples of optional processes for payor entity-users.

In FIG. 7, upon providing the payor entity-user with a plurality of user-selectable options for resources on the user's personalized website location (box 150), the payor entity-user may select an option to access information stored on the system 16 for the specific payor entity, all payor entities, or a predefined group of payor entities to which the specific payor entity belongs. In addition, the payor entity-user may be provided with options for accessing information stored on the system 16 regarding subject-users for which the payor entity is designated and, in some embodiments, other subject-users. The payor entity-user may access, generate or customize reports, for example, as described above with respect to similar activities of the subject-user.

For example, from the payor entity-user's personal website location (box 150 in FIG. 7) or another suitable location on the system 16 website, the payor entity-user may select an option to receive data, reports, software, software updates or other information from the system 16 on the payor entity's computer 22. If the system 16 receives a request from a payor entity-user to receive data, reports, software, software updates or other information (box 152 in FIG. 7), the system 16 may provide the payor entity-user with a list or other arrangement of multiple selectable icons or other indicia representing available data, reports, software, software updates or other information available to the user (box 154 in FIG. 7). When a payor entity-user selects one or more of the icons or other indicia, the system 16 may receive the payor entity-user's request for data, reports, software, software updates or other information (box 156) and transmits the requested information to the payor entity's computer 22 (box 158).

Alternatively, or in addition, some or all of the data, reports, software, software updates or other information available to the payor entity-user may be automatically communicated to the payor entity's computer 22 upon the system 16 receiving a general request to obtain information (box 152) and without the need for the user to receive a list and individually select information items from the list (boxes 154 and 156). Alternatively or in addition, the system 16 and/or the system software 23 residing on the payor entity's computer 22 may be configured to provide the payor entity-user with data, reports, software, software updates or other information automatically during a communication session with the system 16 (without requiring the user to select an option to upload such information in box 152).

As represented by box 160, the system software 23 residing on the payor entity's computer 22 may cause the payor entity's computer to send an acknowledgment message back to the medical data management system 16, and the system 16 may receive such an acknowledgment message over the Internet, for example, upon a successful receipt by the computer 22 of information from the system 16. The payor entity-user may be prompted again to select an activity or resource available on the system 16, for example, by being returned to the payor entity-user's personalized user website location (box 150). Alternatively, or in addition, if no further activities are to be performed with the system 16, the communication session may be ended, as represented by box 162.

By providing the system 16 with the capability to forward data, software, software updates or other information to payor entity-users throughout the system 10, each payor entity-user may be provided with the most updated versions of system software 23 residing on the payor entity's computer 22 and/or the most updated general or subject-specific information. In this manner, the medical data management system may be employed to help manage payor entity-users on the system 10, to provide a more comprehensive and consistent usage of the most appropriate and advanced products and services available to the payor entity-users.

Another optional activity or resource that may be available to the healthcare provider-user may be an option to access payment request information stored on the system 16. As described above, one option available to a healthcare provider-user may be to submit and store payment request information on the system 16, for example, upon providing a healthcare related service to the subject (including, but not limited to a service as described above of accessing subject information, evaluating the information and issuing a new or revised treatment scheme based on the evaluation in an Internet communication environment). Payment request information submitted by the healthcare providers may be stored in appropriate storage locations in the system database 29. The stored payment request information may be associated with one or more designated payor entities, such that designated payor entity-users may have limited access the payment request information in accordance with the access policies of the system 16 (for example, allowing a payor entity access only to payment request information that is associated with that payor entity).

For example, from the payor entity-user's personal website location (box 150 in FIG. 7) or another suitable location on the system 16 website, the payor entity-user may select an option to access payment request information stored on the system 16. If the system 16 receives a request from a payor entity-user to access payment request information (box 164 in FIG. 7), the system 16 may provide the payor entity-user with all payment request information stored in the system database 29 that is associated with the payor entity. For example, the system 16 may provide the payor entity-user with a list or other arrangement of multiple selectable icons or other indicia representing multiple stored payment request information items available to the user (box 166 in FIG. 7), where each payment request item may be a payment request for a service performed by a healthcare provider. When a payor entity-user selects one or more of the icons or other indicia, the system 16 may receive the payor entity-user's request for a payment request information item (box 168) and transmits the requested information to the payor entity's computer 22 (box 170).

As represented by box 172, the system software 23 residing on the payor entity's computer 22 may cause the payor entity's computer to send an acknowledgment message back to the medical data management system 16, and the system 16 may receive such an acknowledgment message over the Internet, for example, upon a successful receipt by the computer 22 of selected payment request information from the system 16. The payor entity-user may be prompted again to select an activity or resource available on the system 16, for example, by being returned to the payor entity-user's personalized user website location (box 150). Alternatively, or in addition, if no further activities are to be performed with the system 16, the communication session may be ended, as represented by box 162.

System Personnel-User Processes

As described above, the data management system 16 may include one or more system personnel, such as customer service operators, system administrators, physicians or other trained medical personnel connected for communication in system 10, via one or more computers or other suitable network devices 18.

Depending upon the role and function of the system personnel, the system 16 may implement suitable access restrictions, allowing the system personnel to access certain information, but not other information. For example, in an embodiment in which the system personnel includes at least one customer service operator who may be contacted by a subject-user for assistance, a customer service operator may be provided with access to some or all of the subject-user information stored on the system 16 database. In further embodiments, the customer service operator may be provided with limited access to information on the system 16, where access is limited to information for the particular subject-user who contacted the customer service operator. In yet further embodiments, such access is provided only if that subject-user authorizes the customer service operator to access the subject-user's information (such as by selecting an authorization icon provided on the subject-user's personalized website location or other suitable website location). In further embodiments, the customer service operator may be provided with access to a subject-user's personalized website location, for example, upon the subject-user authorizing such access as described above. In this manner, a customer service operator may be able to access the same type of information that the subject-user may access and, thus, may better assist a subject-user to address service problems or other operational problems that the subject-user may be experiencing.

Similarly, a customer service operator may be contacted by a healthcare provider-user or a payor-user for assistance. In one example embodiment, the customer service operator may be provided with access to subject information on the system 16, but limited to information for the subject (or group of subjects) who designated that healthcare provider user or that payor-user. In yet a further embodiment, the healthcare provider-user or the payor-user may be required to authorize access by the customer service operator (for example, by selecting an icon from the user's personal website location or other suitable website location), before the system 16 allows the customer service operator access to the subject information for a subject (or group of subjects) who designated that healthcare provider user or that payor-user.

The ability of one or more customer service operators to access information stored on the system 16 can provide significant advantages with respect to a practical operation of the system. Current and historical information stored on the system 16 for a subject-user (or group of subject-users) may be accessed to assist a user. In further embodiments, the customer service operator(s) may also be provided with access to system services that allow the operator to access information from a user's computer (14, 20 and 22) and/or from a subject-user's subject support device (upon, connection of the subject-support, device to a subject-side computer 14 as described above). Such further capabilities may allow a customer service operator to better assist a subject-user with setting or operating a subject support device 12, by allowing the system personnel to view and analyze information received from the subject support device. System operators, administrators or other system personnel may be trained medical personnel, such as physicians. In such embodiments, the medical training of the personnel may be of further benefit to the user.

In further embodiments, system personnel having suitable medical training and/or credentials may be provided with access to subject information on the system 16, for purposes of providing treatment recommendations. In one embodiment, trusted system personnel may have access to some or all subject information on the system 16, including personal subject information and subject identifiers. In other embodiments, system personnel may have access to some or all subject information, but excluding any subject identifiers (to allow the system personnel to evaluate the information without knowledge of the identity of the subject-user(s)

associated with the information). In yet other embodiments, the system personnel may have access to some or all subject information, but only for those subject's for which the system personnel has been authorized to access. Such authorization may be made, for example, by the subject-user(s) associated with the information, the subject-user's healthcare provider or other pre-designated persons.

In such embodiments, authorized system personnel may use a computer or other network device 24 to access and evaluate subject information on the medical data management system 16. Based on an analysis of such information, the system personnel may provide treatment recommendations to a subject-user (or group of subject-users) or to the subject user's (or group's) designated healthcare provider(s). The system 16 may store such treatment recommendations in the system database for access by a subject-user (or group of subject-users) and/or designated healthcare provider-user through a system website. In yet further example embodiments, the system 16 may require review and approval by the subject-user's designated healthcare provider of any treatment recommendations issued by a system 16 personnel, before such treatment recommendations are provided to the subject-user.

Operational Advantages:

Thus, by providing simplified, user-friendly environments, involving the users' own personal computers and conventional Internet connection and browser software, a user may conveniently access a system website and perform a variety of optional activities. Such activities may include sending data from a subject support device (such as an infusion pump, biological sensor or other medical device) to a central database system or receiving messages, programs, program updates, or other information from the management system. Embodiments of the system allow interactive activities between users, such that, for example, a healthcare provider-user may interact online with a subject-user and/or with a payor entity-user, to provide certain healthcare services and/or to request payment for providing healthcare services. Similarly, a payor entity-user may interact online with the system to obtain payment request information and/or other information for verifying payment requests.

A centralized data management system according to embodiments of the invention can provide advantages and improvements with respect to maintaining records, implementing security and privacy measures, making available current and updated software, data and services to all users and other functions that may help to establish compliance with governmental healthcare regulations, industry standards or policies. A centralized system may provide further advantages with respect to collecting aggregate data from a relatively large population of subject-users, for analysis and treatment planning. Subject data for defined groups of subjects may be analyzed to identify trends and improve treatment plans for individual subjects or groups of subjects.

A convenient and user-friendly environment offered by embodiments of the present invention can encourage usage of the system and, thus, improve healthcare management of subjects that, otherwise, may not have received certain healthcare services. For example, the user-friendly environment may encourage subject-users to download data into a system database regularly, so that the subject's updated data (including subject support device data) may be readily available to the subject's healthcare provider or to the subject for retrieval and analysis. Furthermore, selectable user-friendly report formats and the capability to modify or design report formats allow users to obtain subject data from the system in a manner that is most convenient for the user.

Also, a convenient, user-friendly environment for the healthcare provider-user may encourage more comprehensive and more timely reviews of subject information and rendering of appropriate healthcare services. For example, certain healthcare services may be provided from the healthcare provider's own personal computer, including, but not limited to, analyzing a subject's medical information, providing a new or revised treatment scheme to the subject, and forwarding a payment request to a payor entity. In this manner, a healthcare provider may employ a medical data management system according to embodiments of the present invention to provide improved healthcare services to the healthcare provider's subjects. Moreover, an healthcare provider may issue a treatment plan that involves adjustments or modifications to treatments in response to events or activities in the subject's information received from, for example, a subject support device.

A convenient, user-friendly environment can also encourage usage of the system by payor entity-users. In this manner, interactions between healthcare providers, payor entities and subjects may be simplified, by providing convenient procedures for respective users to submit information, and access information under appropriate security and authorization protocols. Thus, for example, a payor entity-user may readily access or automatically receive payment requests issued by healthcare providers for that payor entity. In addition, the payor entity-user may access or automatically receive subject information for subjects associated with payment requests, to allow the payor entity to better evaluate the payment request.

Thus, several features of the system may be employed individually or in combination to improve subject care for individual subject-users. In addition, the system may be employed to collect aggregate data from many different subjects and/or subject support devices (or different defined groups of subjects and/or defined groups of subject support devices). Aggregate data of many subject sources (or groups) may be analyzed to develop best practices for treatment or lifestyle of individual subjects, defined groups of subjects or all subjects. By providing a system with the capability of interfacing with multiple different types of subject support devices, data from different types or different groups of subjects may be obtained by the system, to further improve the aggregate data capabilities of the system. For example, by employing suitable interface software and electronics, subject support devices made from multiple different manufacturers or multiple different models of a subject support device of a given manufacturer may be coupled to communicate with the system, to provide an expanded capability to collect and analyze aggregate data and develop better treatment practices for a greater number of subjects.

Example Website Pages:

The appendix to the present application, which is incorporated herein by reference in its entirety, includes printed copies of example website pages that may be employed in a system 16 website according to embodiments of the present invention. The appendix pages are provided as an example of an embodiment of the invention and are not intended to limit the scope of other embodiments of the invention.

The website pages shown in the appendix relate to a medical data management system configured for diabetes subjects and, thus, is referenced in the website pages as a "diabetes data management system." However, as described above, other embodiments of the invention may be employed for other types of medical conditions or for medical data in general.

Page 1 of the Appendix shows an initial "login" page (which may be the starting page or home page for a system 16 website). The login page includes a location having labeled fields for the user to enter a username and a password and a selectable icon (labeled "Sign In") to allow a user to click and send information entered into the username and password fields to the system 16. The login page also includes a selectable icon (labeled "Sign Up Now") to allow a new user to access (or link to) an enrollment or registration page.

The login page also may include descriptions and/or links to of some of the activities or information that may be available through the website and descriptions and/or links to one or more legal notices, terms of use, a privacy statement and contact information. In Appendix page 1, the example login page includes selectable icons, to link the user to a privacy statement, terms of use and contact information (labeled "Privacy Statement," "Terms of Use," and "Contact Us," respectively). Also, in the example shown on Appendix page 1, the example login page includes selectable icons for linking the user to pages or network sites associated with such resources as a company that produces subject support devices (e.g., MiniMed.com), an instruction or training session (e.g., Pump School Online), and an on-line store that allows a user to order and/or purchase pharmaceuticals and medical equipment such as, but not limited to, replacement infusion sets, insertion tools, insulin supplies, or the like. The icons or links may be selected by a mouse-click, keyboard input, touch screen input or other suitable input operation on the user's computer.

Page 2 of the Appendix shows a "confirmation" page which the system 16 may provide, in response to receiving a user's login information (username and password). The confirmation page includes a request for the user to re-enter the username and password and has a location including fields in which the user may enter that information. The confirmation page also includes a clickable icon, labeled "Continue" that allows the user to send information entered into the username and password fields to the system 16. The confirmation page may also include clickable links to other locations on the website (such as a link to contact information, labeled "Contact Us").

Page 3 of the Appendix shows a "terms of use and privacy statement" page, which includes a description of terms of use of the system 16 and a privacy statement. The page may also include locations, such as labeled fields, in which a user may enter information, such as information confirming that the user (1) is a resident of particular area or country, such as the United States, (2) is over a certain age, such' as over thirteen years of age, and (3) has read, understood and accepted the terms of use and the privacy statement. The page may include selectable icons for allowing a user to accept or decline the terms or statement (labeled "Accept" and "Decline," respectively). The terms of use and privacy statement page may also include clickable links to other locations on the website (such as a link to contact information, labeled "Contact Us"). If the system 16 receives a user's selection of the "Accept" icon, then the system will allow the user to proceed with the access process. If the system 16 receives a user's selection of a "Decline" icon, then the system may end the session and/or link the user to another website, another website location or back to the website home page (for example, Appendix Page 1).

Page 4 of the Appendix shows an "enrollment form" page that may be provided to a website visitor who has selected the "Enroll" icon from the login page (Appendix page 1), to allow a new user to enroll or register with the system 16. The enrollment form page provides locations, including labeled fields, for a user to enter certain contact information, including the user's name (first, last and middle), address, country, telephone number and email address. The enrollment form may also have locations, including labeled fields, for a user to enter additional information that may be relevant to the subject's medical condition (such as, but not limited to, gender, age or age category, diabetes type, or the like). The enrollment form may also include one or more security questions and corresponding security answers. A security question may be selectable from a pre-defined group of security questions (such as questions that ask for the user's mother's maiden name, pet's name or the like). Various selectable security questions may be displayed to the user, as a menu, list or other arrangement, for example, upon the user selecting (for example, clicking on) an appropriate icon on the enrollment form page (such as the arrow to the right of the security question entry field). Security questions may be used by personnel operating the system 16 to verify the authenticity of a user, for example, if a user contacts the system 16 personnel for assistance or if the system 16 personnel contact a user to provide information or respond to a request.

A selectable icon (labeled "Submit") may be provided to allow a user to send an enrollment form with completed subject information, to the system 16. The enrollment form page (as well as other website pages) may also include clickable links to other locations on the website (such as links labeled "Contact Us" and "Privacy Statement-Terms of Use").

Page 5 of the Appendix shows two different website pages that may be provided to website users. The top half of Appendix Page 5 shows an "enrollment completed" page that is provided to a new user, upon successfully completing and sending a new enrollment form (from the enrollment form page on Appendix Page 4). The "enrollment completed" page may include a message informing the user of a successful completion of an enrollment process. The page may also include a selectable icon (labeled "Finish") that may be selected by the user, to return the user to the initial or login page (Appendix Page 1), to allow the user to officially login by entering a username and password. The user name and password may be provided to or selected by a user during the enrollment or registration process.

Upon returning to the initial or login page, the new user may be prompted to change the user's password. The additional security measures of requiring a user to change the password after initial enrollment and before a first use of secure features of the system 16, may provide additional security, for example, in the event that the user's password is compromised during the initial enrollment procedure (e.g., as a result of system administrators, healthcare providers or other individuals or entities assisting the user with the enrollment process).

The bottom half of Appendix Page 5 shows a "password update page" in which a user may change a password. The password update page may include a labeled field or other location in which the user may enter a new password. The page may also include a similar field or location in which the user may enter the password again, to confirm the password.

Appendix Page 6 shows a personal home page that may be provided to a previously enrolled subject-user, upon the subject-user returning to the website through the login procedures described above with respect to Appendix Page 1. The personal home page of the subject may include personalized information, such as the subject's name, and also may include a listing of recent activities. In the illustrated embodiment, the last five activities shown on the example user's personal home page refer to transfers of information from the subject's support devices to the system 16.

The user's personal home page may also provide the user with a plurality of icons for selecting activities available on the website, such as for returning to the home page, for uploading data from a pump or from a meter, for manually entering information or for generating or otherwise accessing reports. In the illustrated example, such selectable icons are provided in the form of tab-shaped icons (labeled "Home", "Upload", "Logbook" and "Reports," respectively). Further labeled icons may be provided to allow a user to select instructions or further descriptions of the activities available for selection. In the illustrated example, such further selectable icons are labeled "Upload Data from My Pump," "Upload Data from My Meter," "Enter Data into My Logbook" and "Generate Reports," respectively. As described below, upon the system 16 receiving a user's selection of tab-like icons (labeled "Home", "Upload", "Logbook" and "Reports," respectively), the system 16 will provide the user with website locations associated with the selected icon, including the home page (shown on Appendix Page 5), a webpage for initiating an upload operation, a webpage for initiating a manual entry into the user's logbook, and a webpage for accessing reports, respectively.

Page 7 of the Appendix shows a "reports available" page that may be provided in response to a user's selection of an icon for generating or otherwise accessing reports (i.e., the "Reports" tab-icon on the webpage shown on the bottom half of Appendix Page 5). The "reports available" page may include a list or other suitable organization of selectable icons representing different types of reports, where different reports may include some or all different information relative to other reports and/or include information in different formats relative to other reports. In the illustrated embodiment, the "reports available" page includes selectable icons in the form of small representations of a page of the report corresponding to the icon and brief descriptions of the report and the type of information contained in the report. Alternatively, or in addition, the "reports available" page may have a location including fields for a user to enter a type of report, a date (or period of dates) for which the data in the report is to encompass and/or a time (or period of times) for which the data in the report is to encompass. The field for the type of report to be generated may include a user-selectable icon (such as the arrow shown to the right of the "Report" field on Appendix Page 6) that, when selected, causes the system 16 to display a list, menu or other suitable arrangement of available reports for selection by the user.

Pages 8 and 9 of the Appendix is a repetitive example Of a "pump settings" report that may be generated by the system 16. Pages 10-14 of the Appendix is a representative example of a "daily summary" report that may be generated by the system 16. Other reports may be generated, depending upon the role, needs and selections of the user. In one example embodiment, a predicted glycemia or a predicted glucose and insulin activity curve may be provided. For example, such curves can show, in a graph, a prediction of the effect on a subject's blood glucose level that a particular event or activity (such as ingestion of a meal) will have. The report may also show actual blood glucose levels (based on sensor or meter readings) and, in some embodiments, may show reprehensive actual blood glucose levels over a defined time period on a graph separate from or in combination with a graph of predicted blood glucose levels over the same time period.

Page 15 of the Appendix shows examples of an initial "upload" page that may be provided in response to a user's selection of an icon for uploading data from a general type of subject support device (i.e., the "Upload" tab-icon on the webpage shown on Appendix Page 6). Upon selecting an option to upload data from one of the selectable general types of subject support devices 12, the system 16 (and/or software 19 or 21) may implement an upload routine (or wizard) for providing a series of instruction pages to assist the user in the upload operation from the selected type of subject support device. Some instruction pages (or each instruction page) may include a request for information and require the user to enter information, where the next instruction page in the series may depend upon the user's input of information. In this manner, different instruction pages may be given to different users, based on the user's input on previous instruction pages, such that a user may be provided with a series of instructions pages that is related to the particular type of subject support device 12 employed by that user.

In the illustrated embodiment, the initial "upload" page on Appendix Page 15 is part of a series of upload instruction pages (examples of which are shown on Appendix Pages 15-22) that provide step-by-step instructions for uploading data from any one of various types of subject support devices 12 that may communicate with the system 16. Each upload instruction page may include an icon (for example, labeled "Next>" in Appendix Pages 15-22) to allow a user to select the next instruction page in the series after the user enters requested information on a current page in the series. Each upload instruction page after the initial upload instruction page may include another icon to allow a user to return to the previous instruction page in the series (where such icon is labeled "Back<" in Appendix Pages 15-22).

The initial "upload" page may include a location for the user to enter information identifying the type of subject support device that will be uploading data to the system 16. In the illustrated embodiment, the user is provided with selectable icons labeled "Insulin Pump" and "Blood Glucose Meter" and is allowed to select one of those icons. Other embodiments may include other suitable selectable icons corresponding to other types of subject support devices. Some or all of the upload instruction pages may include a selectable icon to cancel the upload procedure (where such icon is labeled "Cancel" in Appendix Pages 15-22). Also, some or all of the upload instruction pages may include a selectable icon to allow the user to skip some or all steps, for example, where the user has previously accessed information or provided information required in those steps (where such icon is labeled "Finish" in Appendix Pages 15-22).

In the illustrated example on Appendix Page 15, the user is provided with locations to enter information identifying the general type of subject support device employed by the user. For example, the initial upload page includes selectable text icons that identify, by general common names or descriptions, multiple general types of subject support devices. In the illustrated embodiment, the user is provided with the option of selecting an icon labeled "Insulin Pump" or an icon labeled "Blood Glucose Meter." In further embodiments, other types of subject support devices compatible with the system 16 may be included in the arrangement of selectable icons.

Page 16 of the Appendix shows two further upload instruction pages in the series that may be provided to the user, following the selection of an "Insulin Pump" as the type of subject support device among the selectable icons on Appendix Page 15. The top half of Appendix Page 16 shows a page that may be provided to a user for further refinement of the selection, by allowing the user to select a type of insulin pump (by manufacturer, model, or the like), where the user is provided with selectable icons for selecting one of a plurality of different insulin pump models and/or different manufacturers. The icons may include or otherwise be located adjacent corresponding pictures, photographs, drawings or other suitable representations of the particular types of insulin pumps from which the user may select. By providing photographs or detailed drawings of the plurality of selectable pump options, the user may more easily, visually identify the proper icon that corresponds with the user's pump and thereby reduce any risk of making an erroneous selection.

In the embodiment shown on Appendix Page 16, the user is provided with icons for selecting a type of insulin pump from among a plurality of models of insulin pumps manufactured by a single entity (Medtronic-Minimed). In the illustrated embodiment, the user may select from among three different pumps, identified as Paradigm™ 512/712, Paradigm™ 511 and MiniMed 508. In further embodiments, other pump options may be available. The user may continue to the next page in the series of upload instruction pages by selecting one of the available insulin pump icons and then selecting the Next> icon. Alternatively, the system 16 may automatically provide the next page upon the user selecting one of the available insulin pump icons (i.e., without requiring a further action, such as the selection of the Next> icon).

The bottom half of Appendix Page 16 shows one of the upload instruction pages that may be provided to a user, upon the user selecting one of the icons for a particular insulin pump (i.e., the Paradigm™ 512/712 icon on the page on the top half of Appendix Page 16). The page includes instructions to the user, for example, in the form of a check-list of actions that the user should take with respect to the particular subject support device associated with the selected icon. The user may continue to the next page in the series of upload instruction pages by selecting one of the available insulin pump icons and then selecting the Next> icon. Alternatively, the system 16 may automatically provide the next page upon the lapse of a predetermined time from providing the current page (i.e., without requiring a further action, such as the selection of the Next> icon).

Appendix Page 17 shows another upload instruction page in the series that may be provided to the user, after the user selected one of the icons for an insulin pump (i.e., the Paradigm™ 512/712 icon on the page on the top half of Appendix Page 16). The website page on Appendix Page 17 includes an instruction that requests the user to enter the serial number of the user's insulin pump. The website page also has a location, including a field, in which a user may enter the requested serial number. To assist the user in locating the serial number on the insulin pump, the website page may include a view, such as an enlarged view (picture, photograph, drawing, or other suitable representation) of the portion or side of the selected insulin pump on which the serial number is printed. The viewable representation also includes a marking (such as a circle around the serial number or an arrow pointing to the serial number) directing the user's view to the location of the serial number on the insulin pump. The user may continue to the next page in the series of upload instruction pages by entering a serial number and then selecting the Next> icon. Alternatively, the system 16 may automatically provide the next page upon the user entering a serial number (i.e., without requiring a further action, such as the selection of the Next> icon).

The top half of Appendix Page 18 shows a further upload instruction page in the series that may be provided to the user, after the system 16 received the serial number from a user (as described in the previous website page). In the website page on the top half of Appendix Page 18, the user is provided with an instruction, requesting the user to select a link device (for linking a pump in communication with a computer). The user is also provided with a plurality of icons for selecting a type of link device from among a plurality of link devices. The icons may include or otherwise be located adjacent corresponding pictures, photographs, drawings or other suitable representations of the particular types of link devices from which the user may select. By providing photographs or detailed drawings of the plurality of selectable link options, the user may easily, visually identify the proper icon that corresponds with the user's link device and the risk of making an erroneous selection may be reduced.

In the illustrated embodiment, the user is provided with icons for selecting either a Paradigm Link™ or a Com-Link™ type of link device. However, other embodiments may include other possible link device selections. The user may continue to the next page in the series of upload instruction pages by selecting one of the available link device icons and then selecting the Next> icon. Alternatively, the system 16 may automatically provide the next page upon the user selecting a link device icon (i.e., without requiring a further action, such as the selection of the Next> icon).

The bottom half of Appendix Page 18 shows a page that provides the user with an instruction, requesting the user to make sure that the link device is turned off. The page may include a picture, photograph, drawing or other suitable representation of the selected link device in an off mode (or otherwise showing the user an off button or other operator that places the selected link device in an off mode.

The top half of Appendix Page 19 shows a further upload instruction page in the series that provides an instruction, requesting the user to select a connection type. The user is also provided with a plurality of icons for selecting a type of connection from among a plurality of types of connections. The icons may include or otherwise be located adjacent corresponding pictures, photographs, drawings or other suitable representations of the particular types of connections from which the user may select. By providing photographs or detailed drawings of the plurality of selectable connection options, the user may easily, visually identify the proper icon that corresponds with the user's connection and the risk of making an erroneous selection may be reduced.

In the illustrated embodiment, the user is provided with icons for selecting either a BD-USB connection or a Serial Cable connection. However, other embodiments may include other possible connection selections. The user may continue to the next page in the series of upload instruction pages by selecting one of the available connection icons and then selecting the Next> icon. Alternatively, the system 16 may automatically provide the next page upon the user selecting a connection icon (i.e., without requiring a further action, such as the selection of the Next> icon).

The bottom half of Appendix Page 19 shows a further upload instruction page that provides an instruction, requesting the user to verify that the link cable is properly connected to the selected computer port and to locate the link and pump away from the user's computer. The page also instructs the user to take a further action, such as select the "Finish" icon to cause the system to begin reading (receiving) information from the user's pump.

The top half of Appendix Page 20 shows a message page provided to the user, while the system is configuring itself with appropriate settings, based on the user's input. The bottom half of Appendix page 20 shows a page that provides the user with an instruction, requesting the user to select either an option to choose a serial port or to allow the system to find a port, automatically. In the illustrated embodiment, the user is provided with icons for selecting either "Auto-detect" or "Select port." If the user selects "Select port" icon, then the system may provide the user with a field for entering a port identification and/or a list of possible port identifications from which to choose. The user may continue to the next page in the series of upload instruction pages by selecting an Auto-detect or Select port icon and then selecting the Next> icon. Alternatively, the system 16 may automatically provide the next page upon the user selecting an Auto-detect or Select port icon (i.e., without requiring a further action, such as the selection of the Next> icon).

Page 21 of the Appendix shows two upload instruction pages in the series that may be provided to the user, in the event that the user selected a Blood Glucose Meter type of subject support device from the selectable icons on the website page shown on bottom half of Appendix Page 15. The top half of Appendix Page 21 shows a website page that may be provided to a user for further refinement of the user's selection, by allowing the user to select a type of Blood Glucose Meter (by manufacturer, model, or the like), where the user is provided with selectable icons for selecting one of a plurality of different meter models and/or different meter manufacturers. The icons may include or otherwise be located adjacent corresponding pictures, photographs, drawings or other suitable representations of the particular types of meters from which the user may select.

In the embodiment shown on Appendix Page 21, the user is provided with icons for selecting a type of blood glucose meter from among a plurality of meter manufacturers. In the illustrated embodiment, the user may select from among four different meter manufacturers, identified as Medtronic MiniMed/BD™, Ascensia™/Bayer™, LifeScan™ and MediSense™ or TheraSense™. In other embodiments, other suitable meter manufacturer selections may be provided. The user may continue to the next page in the series of upload instruction pages by selecting one of the available meter manufacturer icons and then selecting the Next> icon. Alternatively, the system 16 may automatically provide the next page upon the user selecting one of the available meter manufacturer icons (i.e., without requiring a further action, such as the selection of the Next> icon).

The bottom half of Appendix Page 21 shows a further upload instruction page in the series that may be provided to a user, upon the user selecting one of the icons for a particular meter manufacturer (i.e., the Medtronic MiniMed/BD meter). The page provides the user with a plurality of icons for selecting a model of the selected manufacturer's meters, for example, a particular model of a Medtronic MiniMed/BD meter, from among a plurality of optional models. The icons may include or otherwise be located adjacent corresponding pictures, photographs, drawings or other suitable representations of the particular models from which the user may select. By providing photographs or detailed drawings of the plurality of selectable model options, the user may easily, visually identify the proper icon that corresponds with the user's meter model and the risk of making an erroneous selection may be reduced.

In the illustrated embodiment, the user is provided with icons for selecting either a Paradigm Link™ or a BD Logic™ model of the selected meter manufacturer. However, other embodiments may include other possible model selections. The user may continue to the next page in the series of upload instruction pages by selecting a model icon and then selecting the Next> icon. Alternatively, the system 16 may automatically provide the next page upon the user selecting a model icon (i.e., without requiring a further action, such as the selection of the Next> icon).

The top half of Appendix Page 22 shows a further upload instruction page in the series that may be provided to the user, following the selection of a type of meter model from the selectable icons on Appendix Page 21. The top half of Appendix Page 22 shows a page that provides the user with an instruction, requesting the user to attach the BD cable to the selected computer port, plug the BD cable connector into the meter strip port and turn the meter off. The website page also instructs the user to take a further action, such as select the "Finish" icon to cause the system to begin reading (receiving) information from the user's meter.

The bottom half of Appendix Page 22 shows an upload instruction page that may be provided to a user, upon the user selecting another one of the icons for a particular meter manufacturer (i.e., the Ascensia/Bayer meter icon) from the options available to the user as shown on the top half of Appendix Page 21. The page provides the user with a plurality of icons for selecting a model of the Ascensia/Bayer meters from among a plurality of optional models. The icons may include or otherwise be located adjacent corresponding pictures, photographs, drawings or other suitable representations of the particular models from which the user may select. By providing photographs or detailed drawings of the plurality of selectable model options, the user may easily, visually identify the proper icon that corresponds with the user's meter model and the risk of making an erroneous selection may be reduced.

In the illustrated embodiment, the user is provided with icons for selecting either a DEX™-DEX™2 or an Elite™-Elite™XL model of the selected meter manufacturer. However, other embodiments may include other possible model selections. The user may continue to the next page in the series of upload instruction pages by selecting a model icon and then selecting the Next> icon. Alternatively, the system 16 may automatically provide the next page upon the user selecting a model icon (i.e., without requiring a further action, such as the selection of the Next> icon).

The top half of Appendix Page 23 shows an upload instruction page that may be provided to a user, upon the user selecting yet another one of the icons for a particular meter manufacturer (i.e., the LifeScan meter icon) from the options available to the user as shown on the top half of Appendix Page 21. The page provides the user with a plurality of icons for selecting a model of the LifeScan meter from among a plurality of optional models. The icons may include or otherwise be located adjacent corresponding pictures, photographs, drawings or other suitable representations of the particular models from which the user may select. By providing photographs or detailed drawings of the plurality of selectable model options, the user may easily, visually identify the proper icon that corresponds with the user's meter model and the risk of making an erroneous selection may be reduced.

In the illustrated embodiment, the user is provided with icons for selecting one of the following LifeScan meter models: One Touch Profile™, One Touch Basic™, One Touch Ultra™, SureStep™ and Fast Take™. However, other embodiments may include other possible model selections. The user may continue to the next page in the series of upload instruction pages by selecting a model icon and then selecting the Next> icon. Alternatively, the system 16 may automatically provide the next page upon the user selecting a model icon (i.e., without requiring a further action, such as the selection of the Next> icon).

The bottom half of Appendix Page 23 shows an upload instruction page that may be provided to a user, upon the user selecting another one of the icons for a particular meter manufacturer (i.e., the TheraSense meter icon) from the options available to the user as shown on the top half of Appendix Page 21. The page provides the user with a plurality of icons for selecting a model of the TheraSense meter from among a plurality of optional models. The icons may include or otherwise be located adjacent corresponding pictures, photographs, drawings or other suitable representations of the particular models from which the user may select. By providing photographs or detailed drawings of the plurality of selectable model options, the user may easily, visually identify the proper icon that corresponds with the user's meter model and the risk of making an erroneous selection may be reduced.

In the illustrated embodiment, the user is provided with icons for selecting either a Precision Xtra™ or a FreeStyle™ model of the selected meter manufacturer. However, other embodiments may include other possible model selections. The user may continue to the next page in the series of upload instruction pages by selecting a model icon and then selecting the Next> icon. Alternatively, the system 16 may automatically provide the next page upon the user selecting a model icon (i.e., without requiring a further action, such as the selection of the Next> icon).

As described above with respect to the Medtronic-Minimed/BD meter, upon selection of an appropriate meter model, the system 16 may provide the user with instructions, requesting the user to attach or check cable connections and to turn off the meter. The system may also instruct the user to take a further action, such as select the "Finish" icon to cause the system to begin reading (receiving) information from the user's meter.

Appendix Pages 24-26 show examples of website pages that may be provided in response to a user's selection of an icon for entering information into the user's logbook (i.e., the "Logbook" tab-icon on the personal website location page shown on Appendix Page 6). The website page shown on the top half of Appendix Page 24 is an example of an initial logbook entry page that may be provided to the user, upon the receipt by the system 16 of a user's selection to enter logbook information.

The initial logbook page (top half of Appendix Page 24) may include a list, a table or other suitable arrangement of information regarding logbook entries made on a particular date. The logbook entry information shown in the table in the illustrated embodiment includes a time associated with each entry, a description of an activity, a value associated with the entry (such as a reference to carbohydrates intake, exercise or other activity and a value associated with that activity, such as grams of carbohydrates or minutes and intensity of exercise) and a comment about some of the activities (such as an indication that a carbohydrate intake entry was associated with a particular meal, or snack). Other activities and associated values, such as urine ketones detection, sleep times and periods, medication ingestion times, infusion set change times or amounts, or the like may be included in the logbook.

A field or other location on the webpage may be provided to allow a user to select the date for which the logbook entries are displayed. In the illustrated embodiment, the date associated with the displayed logbook entries is also displayed on the webpage, near the upper left corner. The webpage may be provided with icons (such as arrows next to the date fields), for allowing a user to select from a plurality of possible dates. Upon a user selection of a date icon, the system 16 may provide the user with a list, menu or other arrangement of selectable date entries.

The initial logbook page (top half of Appendix Page 24) also may provide the user with a location, field or icon for allowing a user to enter logbook information. In the illustrated embodiment, a selectable icon labeled "Add" is provided for a user to initiate a procedure for entering logbook information. In one embodiment, upon selecting an option to add logbook information, the user may be provided with a list, menu or other arrangement of selectable options corresponding to types of entry information. In this manner, the user may be provided with a plurality of selectable icons (in a list, menu or other arrangement), each icon identifying a type of activity for which a user may enter manual information. For example, the user may select an icon for entering information regarding such activities as carbohydrate intakes, exercise activities, HbA1c test results, infusion set changes, sleep times or periods, medication ingestion times, or the like. Other embodiments may include icons for selecting to enter information about other types of logbook activities.

Upon the system 16 receiving a user's selection of a particular type of activity information to enter into a logbook, the system 16 may provide the user with a website page configured to allow the user to enter appropriate information relating to the selected activity. For example, the website page shown on the bottom half of Appendix Page 24 may be provided to a user, upon receipt by the system 16 of a user's selection to enter information regarding carbohydrate intake. The page may provide one or more locations (including fields) for a user to enter particular information. The locations or fields may be labeled with the type of information that the user should enter, such as "Time", "grams" and "Comment."

Similarly, the website page shown on the top half of Appendix Page 25 may be provided to a user, upon receipt by the system 16 of a user's selection to enter information regarding a carbohydrate update. The page may provide one or more locations (including fields) for a user to enter particular information regarding a carbohydrate intake. In the illustrated example, the user is provided with labeled fields for entering a time (hour, minute and am/pm) of the carbohydrate intake, an amount of carbohydrates consumed (grams) and comments (such as an explanation of the type of meal). The bottom half of Appendix Page 25 shows a website page that may be provided to a user, upon receipt by the system 16 of a user's selection to delecte a carbohydrate entry. That page shows information regarding the selected entry to be deleted (including time, amount of carbohydrates and comments) and a message asking the user to verify that the user is sure that the entry should be delected.

The website page shown on the top half of Appendix page 26 may be provided to a user, upon receipt by the system 16 of a user's selection to enter information regarding exercise activities of the subject. The page may provide one or more locations (including fields) for a user to enter particular information regarding one or more exercise activities. The locations or fields may be labeled with the type of information that the user should enter, such as "Time" (for the time of day at which the exercise began or ended), "Minutes" (for the number of minutes the exercise activity occurred), "Intensity" (for an estimated level of the exercise activity) and "Comment" (for any additional information relevant to the activity).

The website page shown on the bottom half of Appendix Page 26 may be provided to a user, upon receipt by the system 16 of a user's selection to enter information regarding HbA1c test activities of the subject. The page may provide one or more locations (including fields) for a user to enter particular information regarding one or more HbA1c test activities. The locations or fields may be labeled with the type of information that the user should enter, such as "Time" (for the time of day at which the test was taken), "HbA1c test results" (for the value of the test results) and "Comment" (for any additional information relevant to the test activity).

The website page shown on Appendix Page 27 may be provided to a user, upon receipt by the system 16 of a user's selection to enter information regarding infusion set changing activities of the subject. The page may provide one or more locations (including fields) for a user to enter particular information regarding one or more infusion set changing activities. The locations or fields may be labeled with the type of information that the user should enter, such as "Time" (for the time of day at which the infusion set was changed) and "Comment" (for any additional information relevant to the infusion set changing activity).

The website pages shown on Appendix Pages 28 and 29 may be provided to a user to allow the user to verify current information stored by the system 16 for the user. Appendix Page 28 shows a "My Info" page, in which various personal information regarding the user is shown, including username, password, security question and answer, name, address, telephone, email, gender, age and diabetes type. Appendix Page 29 shows a "Preferences" page, in which various information regarding the user's blood glucose targets and preferences are provided.

Some or all of the website pages may include user-selectable icons for accessing other website pages (such as the "Home", "Upload", "Logbook" and "Reports" tab-icons shown on the user's personal home page, Appendix Page 6. Alternatively, or in addition, some or all of the website pages may include further selectable icons, for accessing other website pages or locations, including an icon (for example, labeled "My Info") for allowing a user to access (or access and modify) the user's personal information that may have been recorded during the user's registration processes. Other user selectable icons that may be provided on some or all website pages include an icon for allowing a user to view (or view and modify) preferences, an icon for allowing a user to access help information, an icon for allowing a user to access contact information relating to the entity running the system 16, or the like. In the illustrated embodiment, such icons are labeled "Preferences", "Help" and "Contact Us," respectively. Also, some or all of the website pages may include a selectable icon to allow a user to log off of the system (labeled "Log-Off" in the illustrated embodiment).

While embodiments of the present invention described above involve connection to the medical data management system 16, through the Internet, other embodiments may employ other suitable wide area networks. In yet other embodiments involving more limited distribution groups, local area networks may be employed.

The foregoing description of the preferred embodiment of the invention has been presented for the purposes of illustration and description. It is not intended to be exhaustive or to limit the invention to the precise form disclosed. Many modifications and variations are possible in light of the above teachings. Therefore, it is intended that the scope of the invention be limited not by this detailed description, but rather by the claims appended hereto.

What is claimed is:

1. A system for managing medical data on a communication network, the system comprising at least one server connectable for communication on the communication network with at least one healthcare provider computer, at least one computer of an authorized payor entity, and computers of other users, the at least one server being configured for:
   receiving payment request information from the at least one healthcare provider computer, the payment request information being associated with a medical treatment of a first subject by a healthcare provider;
   storing the received payment request information having individual identifiers that identify the first subject in a first storage area of one or more databases, storing medical data having individual identifiers for each of the first subject and a second subject in the first storage area, and storing medical data that is free of individual identifiers for each of the first subject and the second subject in a second storage area of the one or more databases, the medical data being associated with the medical treatment of each of the first subject and the second subject by the at least one healthcare provider;
   providing access to stored payment request information in the first storage area for the authorized payor entity, but not for other users on the communication network;
   providing access to the stored medical data in the first storage area corresponding to the first subject for the authorized payor entity, but not the stored medical data in the first storage area corresponding to the second subject; and
   providing access to the stored medical data corresponding to each of the first and second subjects without the individual identifiers in the second storage area for the authorized payor entity and the other users on the communication network.

2. A system as recited in claim 1, the at least one server being further configured for inhibiting access to stored medical data in the first storage area by other users that are not the authorized payor entity.

3. A system as recited in claim 1, wherein individual identifiers comprise at least one of a subjects name, a subject's address and a subject's work-place.

4. A system as recited in claim 1, the at least one server being further configured for sending a message to the at least one computer of the authorized payor entity, upon receiving the payment request information from the at least one healthcare provider computer, the message indicating that payment request information has been received.

5. A system as recited in claim 4, the at least one server being further configured for receiving a confirmation from the healthcare provider to send the payment request to the authorized payor entity, and sending a message to the at least one computer of the authorized payor entity, in response to receiving the confirmation.

6. A system as recited in claim 1, the at least one server being further configured for receiving the medical data from at least one subject support device with individual identifiers associated with a subject who is using the subject support device.

7. A system as recited in claim 1, wherein the first data storage area and the second data storage area comprise two separate sections of a single data storage device.

8. A system as recited in claim 1, wherein the first data storage area and the second data storage area comprise two separate data storage devices.

9. The system of claim 1, wherein the authorized payor entity is provided access to the individual identifiers stored in the first storage area to identify the first subject of the medical treatment associated with the payment request information.

10. A method for managing medical data on a communication network on which at least one server is connected for communication with at least one healthcare provider computer, at least one computer of an authorized payor entity, and computers of other users, the method comprising:
   receiving payment request information from the at least one healthcare provider computer, the payment request information being associated with a medical treatment of a first subject by a healthcare provider;
   storing the received payment request information having individual identifiers that identify the first subject in a first storage area of one or more databases, storing medical data having individual identifiers for each of the first subject and a second subject in the first storage area, and storing medical data that is free of individual identifiers for each of the first subject and the second subject in a second storage area of the one or more databases, the medical data being associated with the medical treatment of each of the first subject and the second subject by the at least one healthcare provider;
   providing access to stored payment request information in the first storage area for the authorized payor entity, but not for other users on the communication network;
   providing access to the stored medical data in the first storage area corresponding to the first subject for the authorized payor entity, but not the stored medical data in the first storage area corresponding to the second subject; and
   providing access to the stored medical data corresponding to each of the first and second subjects without the individual identifiers in the second storage area for the authorized payor entity and the other users on the communication network.

11. A method as recited in claim 10, further comprising inhibiting access to stored medical data in the first storage area by other users that are not the authorized payor entity.

12. A method as recited in claim 10, wherein individual identifiers comprise at least one of a subjects name, a subject's address and a subject's work-place.

13. A method as recited in claim 10, further comprising sending a message to the at least one computer of the authorized payor entity upon receiving the payment request information from the at least one healthcare provider computer, the message indicating that payment request information has been received.

14. A method as recited in claim 13, further comprising receiving a confirmation from the healthcare provider to send the payment request to the authorized payor entity, and sending a message to the at least one computer of the authorized payor entity, in response to receiving the confirmation.

15. A method as recited in claim 10, further comprising receiving the medical data from at least one subject support device with individual identifiers associated with a subject who is using the subject support device.

16. A method as recited in claim 10, wherein the first data storage area and the second data storage area comprise two separate sections of a single data storage device.

17. A method as recited in claim 10, wherein the first data storage area and the second data storage area comprise two separate data storage devices.

18. A system for managing medical data on a communication network, the system comprising:
   at least one server connectable for communication over the communication network for communication with at least one computer of an authorized payor entity and computers of other users;
   at least one data storage device that stores payment request information with individual identifiers in a first storage area of the at least one data storage device, the payment request information being associated with a medical treatment provided to a first subject, the individual identifiers identifying the first subject;
   the at least one data storage device storing medical data having individual identifiers for each of the first subject and a second subject in the first storage area;
   the at least one data storage device storing medical data that is free of individual identifiers for each of the first subject and the second subject in a second storage area of the at least one data storage device, the medical data being associated with the medical treatment of each of the first subject and the second subject;
   the at least one server providing access to stored payment request information in the first storage area for the authorized payor entity, but not for other users on the communication network;
   the at least one server providing access to the stored medical data in the first storage area corresponding to the first subject for the authorized payor entity, but not the store medical data in the first storage area corresponding to the second subject; and
   the at least one server providing access to the stored medical data corresponding to each of the first and second subjects without the individual identifiers in the second storage area for the authorized payor entity and the other users on the communication network.

19. A system as recited in claim 18, wherein the at least one server inhibits access to stored medical data in the first storage area by other users that are not the authorized payor entity.

20. A system as recited in claim 18, wherein individual identifiers comprise at least one of a subjects name, a subject's address and a subject's work-place.

21. A system as recited in claim 18, wherein the at least one server sends a message to the at least one computer of the authorized payor entity, upon receiving the payment request information, the message indicating that payment request information has been received.

* * * * *